(12) United States Patent
Dyke et al.

(10) Patent No.: US 9,321,740 B2
(45) Date of Patent: Apr. 26, 2016

(54) TETRAZOLE COMPOUNDS AND METHODS OF MAKING AND USING SAME

(75) Inventors: Hazel Joan Dyke, Harlow (GB); Thomas David Pallin, Harlow (GB); Susan Mary Cramp, Harlow (GB)

(73) Assignee: Zafgen, Inc., Boston, MA (US)

( * ) Notice: Subject to any disclaimer, the term of this patent is extended or adjusted under 35 U.S.C. 154(b) by 0 days.

(21) Appl. No.: 13/981,502

(22) PCT Filed: Jan. 26, 2012

(86) PCT No.: PCT/US2012/022721
§ 371 (c)(1),
(2), (4) Date: Jul. 24, 2013

(87) PCT Pub. No.: WO2012/103333
PCT Pub. Date: Aug. 2, 2012

(65) Prior Publication Data
US 2013/0331420 A1 Dec. 12, 2013

Related U.S. Application Data

(60) Provisional application No. 61/436,265, filed on Jan. 26, 2011.

(51) Int. Cl.
*C07D 257/04* (2006.01)
*A61K 31/41* (2006.01)
*C07D 257/06* (2006.01)

(52) U.S. Cl.
CPC .............. *C07D 257/04* (2013.01); *A61K 31/41* (2013.01); *C07D 257/06* (2013.01)

(58) Field of Classification Search
None
See application file for complete search history.

(56) References Cited

U.S. PATENT DOCUMENTS

| | | |
|---|---|---|
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,196,406 A | 3/1993 | Kamei et al. |
| 5,204,345 A | 4/1993 | Kishimoto et al. |
| 5,238,950 A | 8/1993 | Clader et al. |
| 5,288,722 A | 2/1994 | Kishimoto et al. |
| 5,290,807 A | 3/1994 | Folkman et al. |
| 5,422,363 A | 6/1995 | Yanai et al. |
| 5,536,623 A | 7/1996 | Ohmachi et al. |
| 5,698,586 A | 12/1997 | Kishimoto et al. |
| 5,767,293 A | 6/1998 | Oku et al. |
| 5,846,562 A | 12/1998 | Yanai et al. |
| 5,900,431 A | 5/1999 | Molina et al. |
| 6,017,949 A | 1/2000 | D'Amato et al. |
| 6,017,954 A | 1/2000 | Folkman et al. |
| 6,040,337 A | 3/2000 | Hong, II et al. |
| 6,063,812 A | 5/2000 | Hong et al. |
| 6,180,626 B1 | 1/2001 | Shimomura et al. |
| 6,207,704 B1 | 3/2001 | Liu et al. |
| 6,242,494 B1 | 6/2001 | Craig et al. |
| 6,268,387 B1 | 7/2001 | Connor et al. |
| 6,306,819 B1 | 10/2001 | Rupnick et al. |
| 6,323,228 B1 | 11/2001 | BaMaung et al. |
| 6,383,471 B1 | 5/2002 | Chen et al. |
| 6,548,477 B1 | 4/2003 | Olson et al. |
| 6,566,541 B2 | 5/2003 | Liu et al. |
| 6,664,244 B1 | 12/2003 | Furuse et al. |
| 6,803,382 B2 | 10/2004 | Eustache et al. |
| 6,887,863 B2 | 5/2005 | Craig et al. |
| 6,989,392 B2 | 1/2006 | Collins et al. |
| 7,005,440 B1 | 2/2006 | Jayyosi et al. |
| 7,030,262 B2 | 4/2006 | BaMaung et al. |
| 7,084,108 B2 | 8/2006 | Olson et al. |
| 7,115,632 B1 | 10/2006 | Bedell et al. |
| 7,268,111 B2 | 9/2007 | Olson et al. |
| 7,282,588 B2 | 10/2007 | Dhanak et al. |
| 7,288,651 B2 | 10/2007 | Deng et al. |
| 7,297,816 B2 | 11/2007 | Allison et al. |
| 7,396,833 B2 | 7/2008 | Xie et al. |
| 7,491,718 B2 | 2/2009 | Comess et al. |
| 7,718,695 B2 | 5/2010 | Kim et al. |
| 8,119,663 B2 | 2/2012 | Heimbach et al. |
| 8,367,721 B2 | 2/2013 | Hughes et al. |
| 2002/0002152 A1 | 1/2002 | Craig et al. |
| 2004/0019113 A1 | 1/2004 | Josefiak et al. |
| 2004/0067266 A1 | 4/2004 | Toppo |
| 2004/0068012 A1 | 4/2004 | Comess et al. |
| 2004/0116495 A1 | 6/2004 | Marino, Jr. et al. |
| 2004/0157836 A1 | 8/2004 | Comess et al. |
| 2004/0167128 A1 | 8/2004 | Comess et al. |
| 2004/0204472 A1 | 10/2004 | Briggs et al. |
| 2005/0037994 A1 | 2/2005 | Kim et al. |

(Continued)

FOREIGN PATENT DOCUMENTS

| | | |
|---|---|---|
| EP | 0682020 A1 | 11/1995 |
| WO | WO-98/38859 | 9/1998 |

(Continued)

OTHER PUBLICATIONS

U.S. Appl. No. 14/372,877, filed Jul. 17, 2014.
U.S. Appl. No. 14/372,893, filed Jul. 17, 2014.
Anderson, "The Use of Fumagillin in Amoebiasis" Ann NY Acad Sci. Dec. 30, 1952;55(6):1118-24.
Benny, et al., "An Orally Delivered Small-Molecule Formulation with Antiangiogenic and Anticancer Activity" Nat Biotechnol Jul. 2008;26(7):799-807. doi: 10.1038/nbt1415. Epub Jun. 29, 2008.
Bernier, et al., "Fumagillin class inhibitors of methionine aminopeptidase-2" Drugs of the Future 2005 30(5): 497-500.

(Continued)

*Primary Examiner* — Alicia L Otton
(74) *Attorney, Agent, or Firm* — Goodwin Procter LLP

(57) ABSTRACT

Described herein are tetrazole compounds and their use in treating medical disorders, such as obesity. Pharmaceutical compositions and methods of making various tetrazole compounds are provided. The compounds are contemplated to have activity against methionyl aminopeptidase 2.

10 Claims, No Drawings

(56) References Cited

U.S. PATENT DOCUMENTS

| | | |
|---|---|---|
| 2005/0239878 A1 | 10/2005 | Thompson et al. |
| 2006/0045865 A1 | 3/2006 | Jacob et al. |
| 2006/0069161 A1 | 3/2006 | Lee et al. |
| 2006/0276512 A1 | 12/2006 | Han et al. |
| 2007/0078172 A1 | 4/2007 | McElroy et al. |
| 2008/0200402 A1 | 8/2008 | Alvinerie et al. |
| 2008/0312231 A1 | 12/2008 | Merla et al. |
| 2009/0088437 A1 | 4/2009 | Xie et al. |
| 2009/0148396 A1 | 6/2009 | Akullian et al. |
| 2010/0016425 A1 | 1/2010 | Vath |
| 2010/0111894 A1 | 5/2010 | Benny-Ratsaby et al. |
| 2010/0158855 A1 | 6/2010 | Benny-Ratsaby et al. |
| 2012/0004162 A1 | 1/2012 | Vath |
| 2012/0010259 A1 | 1/2012 | Vath |
| 2012/0010290 A1 | 1/2012 | Vath |
| 2013/0053364 A1 | 2/2013 | Dyke et al. |
| 2013/0123235 A1 | 5/2013 | Clark et al. |
| 2013/0217759 A1 | 8/2013 | Zahler et al. |
| 2013/0331420 A1 | 12/2013 | Dyke et al. |
| 2014/0073623 A1 | 3/2014 | Cramp et al. |
| 2014/0080822 A1 | 3/2014 | Cramp et al. |
| 2014/0088078 A1 | 3/2014 | Cramp et al. |

FOREIGN PATENT DOCUMENTS

| | | |
|---|---|---|
| WO | WO-99/57097 | 11/1999 |
| WO | WO-99/59986 A1 | 11/1999 |
| WO | WO-99/59987 A1 | 11/1999 |
| WO | WO-00/64876 A1 | 11/2000 |
| WO | WO-01/24796 A1 | 4/2001 |
| WO | WO-02/26782 A2 | 4/2002 |
| WO | WO-02/059124 A2 | 8/2002 |
| WO | WO-02/083065 A2 | 10/2002 |
| WO | WO-03/027104 A1 | 4/2003 |
| WO | WO-2004/033419 A1 | 4/2004 |
| WO | WO-2005/025554 A2 | 3/2005 |
| WO | WO-2005/082349 A1 | 9/2005 |
| WO | WO-2005/113513 A2 | 12/2005 |
| WO | WO-2006/080591 A1 | 8/2006 |
| WO | WO 2008/008374 * | 1/2008 |
| WO | WO-2008/008374 A2 | 1/2008 |
| WO | WO-2008/131947 A1 | 11/2008 |
| WO | WO-2009/009501 A2 | 1/2009 |
| WO | WO-2009/073445 A2 | 6/2009 |
| WO | WO-2010/042163 A2 | 4/2010 |
| WO | WO-2010/048499 A1 | 4/2010 |
| WO | WO-2010/065877 A2 | 6/2010 |
| WO | WO-2010/065879 A2 | 6/2010 |
| WO | WO-2010/065881 A2 | 6/2010 |
| WO | WO-2010/065883 A2 | 6/2010 |
| WO | WO-2011/044506 A2 | 4/2011 |
| WO | WO-2011/085198 A1 | 7/2011 |
| WO | WO-2011/088055 A2 | 7/2011 |
| WO | WO-2011/127304 A2 | 10/2011 |
| WO | WO-2011/150338 A1 | 12/2011 |
| WO | WO-2012/012642 A1 | 1/2012 |
| WO | WO-2012/051318 A1 | 4/2012 |
| WO | WO-2012/064838 A1 | 5/2012 |
| WO | WO-2012/064928 A1 | 5/2012 |
| WO | WO-2012/074968 A1 | 6/2012 |
| WO | WO-2012/075020 A1 | 6/2012 |
| WO | WO-2012/075026 A1 | 6/2012 |
| WO | WO-2012/103333 A1 | 8/2012 |
| WO | WO-2012/154676 A1 | 11/2012 |
| WO | WO-2012/154678 A1 | 11/2012 |
| WO | WO-2012/154679 A1 | 11/2012 |
| WO | WO-2013/033430 A1 | 3/2013 |

OTHER PUBLICATIONS

Brakenhielm, et al., "Angiogenesis Inhibitor, TNP-470, Prevents Diet-Induced and Genetic Obesity in Mice" Circ Res. Jun. 25, 2004;94(12):1579-88. Epub May 20, 2004.

Braunwald, et al., "Obesity" in Harrison's Principles of Internal Medicine, 15th Ed., 479-86 2001.

Chan, et al. "Discovery of thiophene-2-carboxylic acids as potent inhibitors of HCV NS5B polymerase and HCV subgenomic RNA replication. Part 1: Sulfonamides" Bioorg Med Chem Lett. Feb. 9, 2004;14(3):793-6.

Chun et al. "Novel inhibitors targeted to methionine aminopeptidase 2 (MetAP2) strongly inhibit the growth of cancers in xenografted nude model" Int J Cancer. Mar. 10, 2005;114(1):124-30.

Database Registry [Online] (Apr. 18, 2001), Chemical Abstracts Service, XP002664465.

Database Registry [Online] (Nov. 10, 2004), Chemical Abstracts Service, XP002664464.

Database Registry [Online] (Apr. 13, 2007), Chemical Abstracts Service, XP002664462.

Database Registry [Online] (Aug. 24, 2008), Chemical Abstracts Service, XP002664461.

Database Registry [Online] (Jan. 20, 2009), Chemical Abstracts Service, XP002664460.

Database Registry [Online] (Jan. 23, 2009), Chemical Abstracts Service, XP002664459.

Database Registry [Online] (Jan. 27, 2009), Chemical Abstracts Service, XP002664458.

Database Registry [Online] (Sep. 15, 2009), Chemical Abstracts Service, XP002664454.

Database Registry [Online], (Sep. 11, 2009) Chemical Abstracts Service, XP002664455.

Database Registry [Online], (Oct. 4, 2010) Chemical Abstracts Service, XP002664453.

Database Registry [Online] (Jun. 7, 2009) Chemical Abstracts Service, XP002664456.

Database Registry [Online] (Jan. 28, 2009) Chemical Abstracts Service, XP002664457.

Database Registry [Online] (Mar. 13, 2007), Chemical Abstracts Service, XP002664463.

Didier, et al., "Antimicrosporidial Activities of Fumagillin, TNP-470, Ovalicin, and Ovalicin Derivatives in Vitro and In Vivo" Antimicrob Agents Chemother. Jun. 2006;50(6):2146-55.

DiPaolo, et al. "Studies on the Carcinolytic Activity of Fumagillin and Some of its Derivatives" Antibiot Annu. 1958-1959;6:541-6.

Drevs, et al. "Antiangiogenic Potency of FK866/K22.175, a New Inhibitor of Intracellular NAD Biosynthesis, In Murine Renal Cell Carcinoma" Anticancer Res. Nov.-Dec. 2003;23(6C):4853-8.

Dumas, et al., "Synthesis and Structure Activity Relationships of Novel Small Molecule Cathepsin D Inhibitors" Bioorg Med Chem Lett. Sep. 6, 1999;9(17):2531-6.

Eder, et al., "Phase 1 Dose Escalation Safety & Tolerance Study of PPI-2458 in Subjects with Non-Hodgkin's Lymphoma or Solid Tumors" (Presented on Nov. 7-10, 2006 at EORTC-NCI-AACR Symposium on "Molecular Targets and Cancer Therapeutics."), 2006.

European Search Report for EP 09798793 dated Oct. 11, 2011, 9 pages.

Everhart "Contributions of Obesity and Weight Loss to Gallstone Disease" Ann Intern Med. Nov. 15, 1993;119(10):1029-35.

Garrabrant, et al., "Small molecule inhibitors of methionine aminopeptidase type 2 (MetAP-2) fail to inhibit endothelial cell proliferation or formation of microvessels from rat aortic rings in vitro" Angiogenesis. 2004;7(2):91-6.

Han, et al., "Design and Synthesis of Highly Potent Fumagillin Analogues from Homology Modeling for a Human MetAP-2" Bioorg Med Chem Lett. Jan. 3, 2000;10(1):39-43.

Hughes et al. "Ascending dose-controlled trial of beloranib, a novel obesity treatment for safety, tolerability, and weight loss in obese women" Obesity (Silver Spring). Sep. 2013;21(9):1782-8. doi: 10.1002/oby.20356. Epub May 25, 2013.

Ingber, et al., "Synthetic analogues of fumagillin that inhibit angiogenesis and suppress tumour growth" Nature. Dec. 6, 1990;348(6301):555-7.

Jeong, et al., "Total Synthesis and Antiangiogenic Activity of Cyclopentane Analogues of Fumagillol" *Bioorg Med Chem Lett*. Aug. 1, 2005;15(15):3580-3.

(56) References Cited

OTHER PUBLICATIONS

Kawai, et al., "Development of sulfonamide compounds as potent methionine aminopeptidase type II inhibitors with antiproliferative properties". Bioorg Med Chem Lett. Jul. 1, 2006;16(13):3574-7. Epub May 2, 2006.

Kim et al., "Development of parenteral formulation for a novel angiogenesis inhibitor, CKD-732 through complexation with hydroxypropyl-beta-cyclodextrin" Int J Pharm. Mar. 19, 2004;272(1-2):79-89.

Kim et al., "General pharmacology of CKD-732, a new anticancer agent: effects on central nervous, cardiovascular, and respiratory system," Biol Pharm Bull. Feb. 2005;28(2):217-23.

Kim, et al., "Assessment of the Anti-Obesity Effects of the TNP-470 Analog, CKD-732," J Mol Endocrinol. Apr. 2007;38(4):455-65.

Kruger "TNP-470: An Angiogenesis Inhibitor in Clinical Development for Cancer," Expert Opin Investig Drugs. Jun. 2000;9(6):1383-96.

Lee et al., "Absorption, distribution, metabolism, and excretion of CKD-732, a novel antiangiogenic fumagillin derivative, in rats, mice, and dogs," Arch Pharm Res. Feb. 2004;27(2):265-72.

Lee et al.,"Selective N-Demethylation of Tertiary Aminofumagillols with Selenium Dioxide via a Non-classical Polonovski Type Reaction" *Heterocycles* vol. 68, No. 5, 2006, pp. 915-932.

Lee et al., "Design, Synthesis, and Antiangiogenic Effects of a Series of Potent Novel Fumagillin Analogues" Chem Pharm Bull (Tokyo). Jul. 2007;55(7):1024-9.

Lijnen et al., "Fumagillin Reduces Adipose Tissue Formation in Murine Models of Nutritionally Induced Obesity" Obesity (Silver Spring). Dec. 2010;18(12):2241-6. doi: 10.1038/oby.2009.503. Epub Jan. 21, 2010.

Makosza et al. "Reaction of organic anions. 131. Vicarious nucleophilic substitution of hydrogen in nitrobenzoic acids" Makosza, M.; Ludwiczak, S. Dep. Chem.,Tech. Univ. Warsaw, Warsaw, Pol. Synthesis (1986), (1), 50-2. CODEN: SYNTBF ISSN: 0039-7881. Journal written in English. CAN 105:171971 AN 1986:571971 CAPLUS (Copyright (C) 2009 ACS on SciFinder (R)).

Masiero et al. "New Anti-angiogenesis Agents: Review of the Clinical Experience with Carboxyamido-Triazole (CAI), Thalidomide, TNP-470 and Interleukin-12" Angiogenesis. 1997;1(1):23-35.

McCowan, et al., "Fumagillin (H-3), a New Antibiotic with Amebicidal Properties" Science. Feb. 23, 1951;113(2930):202-3.

Milkowski, Deborah M., et al., Antiangiogenic Agents in Cancer Therapy, Chapter 22 "TNP-470," pp. 385-398, 2012.

Molina et al., "Potential Efficacy of Fumagillin in Intestinal Microsporidiosis Due to Enterocytozoon Bieneusi in Patients with HIV Infection: Results of a Drug Screening Study" AIDS. Nov. 1997;11(13):1603-10.

Molina et al., "Fumagillin Treatment of Intestinal Microsporidiosis" N Engl J Med. Jun. 20, 2002;346(25):1963-9.

Molina, et al., "Trial of Oral Fumagillin for the Treatment of Intestinal Microsporidiosis in Patients with HIV Infection" AIDS. Jul. 7, 2000;14(10):1341-8.

Myung et al., "The identification of in vitro metabolites of CKD-732 by liquid chromatography/tandem mass spectrometry" Rapid Commun Mass spectrom. 2002;16(21):2048-53.

Naganuma et al., "Metronomic Doxifluridine Chemotherapy Combined with the Anti-Angiogenic Agent TNP=470 Inhibits the Growth of Human Uterine Carcinosarcoma Xenografts" Cancer Sci. Aug. 2011;102(8):1545-52. doi: 10.1111/j.1349-7006.2011.01998.x. Epub Jul. 3, 2011.

National Task Force on the Prevention and Treatment of Obesity "Very Low-Calorie Diets," JAMA. Aug. 25, 1993;270(8):967-74.

Noel et al., "Increased Risk of Acute Pancreatitis and Biliary Disease Observed in Patients with Type 2 Diabetes" Diabetes Care. May 2009;32(5):834-8. doi: 10.2337/dc08-1755. Epub Feb. 10, 2009.

Pagliarulo et al., "Gallstone disease and related risk factors in a large cohort of diabetic patients" Dig Liver Dis. Feb. 2004;36(2):130-4.

Patra et al., "Regiospecific Synthesis of Benzo[b]fluorenones via Ring Contraction by Benzil-Benzilic Acid Rearrangement of Benz[a]anthracene-5,6-diones" Synthesis 2006, (15), 2556-2562.

International Search Report and Written Opinion for International Application No. PCT/US2011/044864, mailed on Oct. 7, 2011, 7 pages.

International Search Report and Written Opinion for International Application No. PCT/US2010/052050, mailed Mar. 25, 2011, 11 pages.

International Search Report and Written Opinion for International Application No. PCT/US2012/022721, mailed on Mar. 29, 2012, 9 pages.

International Search Report for International Application No. PCT/US2012/036789, mailed Jul. 17, 2012, 4 pages.

International Search Report for International Application No. PCT/US2012/036792, mailed on Jun. 27, 2012 (3 pages).

International Search Report for International Application No. PCT/US2012/036793, mailed on Jun. 21, 2012, 4 pages.

Written Opinion for International Application No. PCT/US2009/066811, mailed on Sep. 1, 2010, 3 pages.

International Search Report and Written Opinion for International Application No. PCT/US2011/055987, mailed Jan. 16, 2012, 24 pages.

International Search Report and Written Opinion for International Application No. PCT/US2013/021919, mailed Mar. 25, 2013, 14 pages.

International Search Report and Written Opinion for International Application No. PCT/US2013/021914, mailed Apr. 18, 2013, 12 pages.

Picoul et al., "Progress in fumagillin synthesis" Pure Appl. Chem., vol. 75, Nos. 2-3, pp. 235-249, 2003.

Rhee et al., "Angiogenesis inhibitor attenuates parathyroid hormone-induced anabolic effect" Biomed Pharmacother. Jan. 2009;63(1):63-8. doi: 10.1016/j.biopha.2007.10.013. Epub Nov. 20, 2007.

Rupnick "Adipose Tissue Mass Can be Regulated Through the Vasculature" Proc Natl Acad Sci U S A. Aug. 6, 2002;99(16):10730-5. Epub Jul. 29, 2002.

Sankar et al., "2-[1-(Phenylsulfonyl)ethyl]benzoic acid and 2-[1-(phenylsulfonyl)propyl]benzoic acid" Acta Crystallogr C. May 2002;58(Pt 5):o257-9. Epub Apr. 11, 2002.

Seneca et al., "Amebiasis: a review. II. Laboratory diagnosis, differential diagnosis and therapy" Am J Dig Dis. Jul. 1956;1(7):310-22.

Sheppard et al., "3-Amino-2-hydroxyamides and related compounds as inhibitors of methionine aminopeptidase-2" Bioorg Med Chem Lett. Feb. 23, 2004;14(4):865-8.

Sheppard et al., "Discovery and Optimization of Anthranilic Acid Sulfonamides as Inhibitors of Methionine Aminopeptidase-2: A Structural Basis for the Reduction of Albumin Binding" J Med Chem. Jun. 29, 2006;49(13):3832-49.

Shin et al., "A Phase Ib pharmacokinetic study of the anti-angiogenic agent CKD-732 used in combination with capecitabine and oxaliplatin (XELOX) in metastatic colorectal cancer patients who progressed on irinotecan-based chemotherapy" Invest New Drugs. Apr. 2012;30(2):672-80. doi: 10.1007/s10637-010-9625-x. Epub Dec. 29, 2010.

Shin "A phase I pharmacokinetic and pharmacodynamic study of CKD-732, an antiangiogenic agent, in patients with refractory solid cancer" Invest New Drugs. Oct. 2010;28(5):650-8. doi: 10.1007/s10637-009-9287-8. Epub Jul. 8, 2009.

Shvedov et al., "Functional Derivatives of Thiophene" Chemistry of Heterocyclic Compounds Feb. 1977, vol. 13, Issue 2, pp. 163-165.

Siddiqui et al., "The Presence of Substituents on the Aryl Moiety of the Aryl Phosphoramidate Derivative of d4T Enhances Anti-HIV Efficacy in Cell Culture: A Structure-Activity Relationship" *J Med Chem.* Feb. 11, 1999;42(3):393-9.

Srikumar et al., "Structural Insights on Brugia Malayi Transglutaminase With Cinnamoyl Derivatives—A Molecular Docking Approach" Int J Pharm Bio Sci Jul. 2012; 3(3): (B) 998-1006.

Teicher, et al., "Antiangiogenic Agents in Cancer Therapy" pp. 385-398, 1999.

Thirumamagal, et al., "Formation of 2-arylindane-1,3-diones and 3-alkylphthalides from methyl o-[ -phenylsulfonyl]toluate" Tetrahedron Letters (2008), 49(3), 512-515.

Wang, et al., "Lead optimization of methionine aminopeptidase-2 (MetAP2) inhibitors containing sulfonamides of 5, 6-disubstituted

(56) References Cited

OTHER PUBLICATIONS anthranilic acids" Bioorg Med Chem Lett. May 15, 2007;17(10):2817-22. Epub Feb. 25, 2007.

Wang, et al., "Tumor Suppression by a Rationally Designed Reversible Inhibitor of Methionine Aminopeptidase-2" Cancer Res. Nov. 15, 2003;63(22):7861-9.

Wang et al. "Correlation of tumor growth suppression and methionine aminopetidase-2 activity blockade using an orally active inhibitor" *Proc Natl Acad Sci U S A*. Feb. 12, 2008;105(6):1838-43. doi: 10.1073/pnas.0708766105. Epub Feb 5, 2008.

Weinsier et al., "Gallstone Formation and Weight Loss" Obes Res. Jan. 1993;1(1):51-6.

Weinsier, et al., "Medically Safe Rate of Weight Loss for the Treatment of Obesity: A Guideline Based on Risk of Gallstone Formation" Am J Med. Feb. 1995;98(2):115-7.

Winter et al., "Endothelial $\alpha_v\beta_3$ Integrin-Targeted Fumagillin Nanoparticles Inhibit Angiogenesis in Atherosclerosis," Arterioscler Thromb Vasc Biol. Sep. 2006;26(9):2103-9. Epub Jul. 6, 2006.

Yanai, et al., "Antitumor Effect of Arterial Administration of a Medium-Chain Triglyceride Solution of an Angiogenesis Inhibitor, TNP-470, in Rabbits Bearing VX-2 Carcinoma" Pharm Res. May 1995;12(5):653-7.

Yanai, et al., "Antitumor activity of a medium-chain triglyceride solution of the angiogenesis inhibitor TNP-470 (AGM-1470) when administered via the hepatic artery to rats bearing Walker 256 carcinosarcoma in the liver" J Pharmacol Exp Ther. Dec. 1994;271(3):1267-73.

European Examination Report for European Patent Application No. 12704958.3, mailed Jun. 20, 2014, 4 pages.

\* cited by examiner

TETRAZOLE COMPOUNDS AND METHODS OF MAKING AND USING SAME

CROSS-REFERENCE TO RELATED APPLICATIONS

This application is the national stage of International (PCT) Patent Application Serial No. PCT/US2012/022721, filed Jan. 26, 2012, and published under PCT Article 21(2) in English, which claims the benefit of and priority to U.S. Provisional Patent Application No. 61/436,265 filed Jan. 26, 2011, the entire disclosures of each of which are hereby incorporated by reference in their entirety.

BACKGROUND

Over 1.1 billion people worldwide are reported to be overweight. Obesity is estimated to affect over 90 million people in the United States alone. Twenty-five percent of the population in the United States over the age of twenty is considered clinically obese. While being overweight or obese presents problems (for example restriction of mobility, discomfort in tight spaces such as theater or airplane seats, social difficulties, etc.), these conditions, in particular clinical obesity, affect other aspects of health, i.e., diseases and other adverse health conditions associated with, exacerbated by, or precipitated by being overweight or obese. The estimated mortality from obesity-related conditions in the United States is over 300,000 annually (O'Brien et al. Amer J Surgery (2002) 184:4S-8S; and Hill et al. (1998) Science, 280:1371).

There is no curative treatment for being overweight or obese. Traditional pharmacotherapies for treating an overweight or obese subject, such as serotonin and noradrenergic re-uptake inhibitor, noradrenergic re-uptake inhibitors, selective serotonin re-uptake inhibitors, intestinal lipase inhibitors, or surgeries such as stomach stapling or gastric banding, have been shown to provide minimal short-term benefits or significant rates of relapse, and have further shown harmful side-effects to patients.

MetAP2 encodes a protein that functions at least in part by enzymatically removing the amino terminal methionine residue from certain newly translated proteins such as glyceraldehyde-3-phosphate dehydrogenase (Warder et al. (2008) *J Proteome Res* 7:4807). Increased expression of the MetAP2 gene has been historically associated with various forms of cancer. Molecules inhibiting the enzymatic activity of MetAP2 have been identified and have been explored for their utility in the treatment of various tumor types (Wang et al. (2003) Cancer Res 63:7861) and infectious diseases such as microsporidiosis, leishmaniasis, and malaria (Zhang et al. (2002) J Biomed Sci. 9:34). Notably, inhibition of MetAP2 activity in obese and obese-diabetic animals leads to a reduction in body weight in part by increasing the oxidation of fat and in part by reducing the consumption of food (Rupnick et al. (2002) Proc Natl Acad Sci USA 99:10730).

Such MetAP2 inhibitors may be useful as well for patients with excess adiposity and conditions related to adiposity including type 2 diabetes, hepatic steatosis, and cardiovascular disease (via e.g. ameliorating insulin resistance, reducing hepatic lipid content, and reducing cardiac workload). Accordingly, compounds capable of modulating MetAP2 are needed to address the treatment of obesity and related diseases as well as other ailments favorably responsive to MetAP2 modulator treatment.

SUMMARY

Described herein are, for example, compounds which may be modulators of MetAP2, use of the compounds as medicinal agents, processes for the preparation of the compounds, pharmaceutical compositions containing one or more of the compounds as active ingredients both alone or in combination with other agents, and use of the compounds in the manufacture of medicaments for the use in the inhibition of MetAP2 activity in warm-blooded animals such as humans. In some embodiments, the compounds may be useful for the treatment of obesity, type 2 diabetes, and/or other obesity-associated conditions. Also provided are pharmaceutical compositions comprising at least one disclosed compound and a pharmaceutically acceptable carrier.

In an embodiment, provided herein are compounds represented by Formula I:

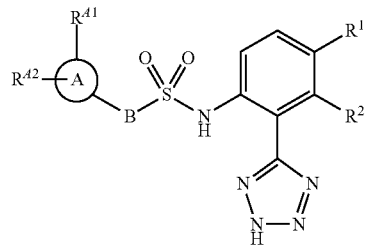

and pharmaceutically acceptable salts, stereoisomers, esters, and prodrugs thereof, wherein:

A is a ring selected from the group consisting of phenyl, heteroaryl, $C_{3-6}$cycloalkyl, and heterocyclyl, wherein heteroaryl is a 5-6 membered ring having one, two, or three heteroatoms each independently selected from N, O, or S, wherein heterocyclyl is a 4-7 membered ring; B is selected from the group consisting of a bond or $(CR^{B1}R^{B2})$;

$R^1$ is selected from the group consisting of hydrogen, halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— where w is 0, 1, or 2, heteroaryl, heterocyclyl, heterocyclyloxy, heterocyclyl-$C_{1-6}$alkyl, and heterocyclyl-$C_{1-6}$alkoxy, wherein heteroaryl is a 5-6 membered ring having one, two, or three heteroatoms each independently selected from N, O, or S, wherein heteroaryl is optionally substituted with one or more substituents each independently selected from $R^b$, wherein heterocyclyl is a 4-7 membered ring optionally substituted by one or more substituents each independently selected from $R^c$, and wherein when heterocyclyl contains a —NH— moiety, that —NH— moiety is optionally substituted by $R^d$, wherein $C_{2-6}$alkenyl, $C_{2-6}$alkynyl, $C_{3-6}$alkenyloxy, and $C_{3-6}$alkynyloxy are each independently optionally substituted by one or more substituents each independently selected from $R^p$, wherein $C_{1-6}$alkyl and $C_{1-6}$alkoxy are each independently optionally substituted by one or more substituents each independently selected from $R^{p'}$, wherein $C_{3-6}$cycloalkyl and $C_{3-6}$cycloalkoxy are each independently optionally substituted by one or more substituents each independently selected from $R^{p''}$;

$R^2$ is selected from the group consisting of halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkyloxy, $C_{1-6}$alkyl-S(O)$_2$—, $C_{3-6}$cycloalkyl-$C_{1-4}$alkyl-, $C_{3-6}$cycloalkyl-$C_{1-4}$alkoxy-, phenyl-$C_{1-6}$alkyl-, phenyl, phenoxy, phenyl-$C_{1-6}$alkoxy-, heteroaryl, heteroaryloxy, heteroaryl-$C_{1-6}$alkyl, heteroaryl-$C_{1-6}$alkoxy, heterocyclyl-$C_{1-6}$alkyl-, and heterocyclyl-$C_{1-6}$alkoxy-, wherein heteroaryl is a 5-6 membered ring having one, two, or three heteroatoms each independently selected from N, O, or S, wherein heteroaryl and phenyl group are each independently optionally substituted with one or more substituents each independently selected from $R^b$, wherein heterocyclyl is a 4-7 membered ring optionally substituted by one or more substituents each independently selected from $R^c$, and wherein when heterocyclyl contains a —NH— moiety, that —NH— moiety is optionally substituted by $R^d$, wherein $C_{1-6}$alkyl, $C_{2-6}$alkenyl, $C_{2-6}$alkynyl, $C_{1-6}$alkoxy, $C_{3-6}$alkenyloxy, and $C_{3-6}$alkynyloxy are each independently optionally substituted by one or more substituents each independently selected from halogen, hydroxyl, $R^aR^{a'}N$—, and cyano, wherein $C_{3-6}$cycloalkyl, and $C_{3-6}$cycloalkoxy are each independently optionally substituted by one or more substituents each independently selected from halogen, hydroxyl, $R^aR^{a'}N$—, cyano, and $C_{1-6}$alkyl; or $R^1$ and $R^2$ when taken together with the carbons to which they are attached form a 5-7 membered saturated, partially unsaturated, or unsaturated ring, optionally having 1, 2, or 3 groups each independently selected from O, $NR^h$, and $S(O)_r$ where r is 0, 1, or 2, wherein the 5-7 membered ring is optionally substituted on a carbon by one or more groups each independently selected from $R^e$;

$R^{A1}$ is selected, independently for each occurrence, from the group consisting of hydrogen, hydroxyl, cyano, halogen, $C_{1-6}$alkyl, $C_{2-6}$alkenyl, $C_{3-6}$alkynyl, $C_{3-6}$cycloalkyl, $C_{1-6}$alkoxy, and $R^fR^gN$—, wherein $C_{1-6}$alkyl, $C_{2-6}$alkenyl, $C_{3-6}$alkynyl, $C_{3-6}$cycloalkyl, and $C_{1-6}$alkoxy are each independently optionally substituted with one or more halogens;

$R^{A2}$ is selected, independently for each occurrence, from the group consisting of hydrogen, hydroxyl, cyano, halogen, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— where w is 0, 1, or 2, $R^fR^gN$—, $R^fR^gN$-carbonyl-, $R^fR^gN$-carbonyl-$N(R^a)$—, $R^fR^gN$—$SO_2$—, $C_{1-6}$alkyl-carbonyl-$N(R^a)$—, $C_{1-6}$ alkylsulfonylN$(R^a)$—, $C_{1-6}$alkoxycarbonyl-$N(R^a)$—, phenyl, phenoxy, phenyl-$C_{1-6}$alkyl-, phenyl-$C_{1-6}$alkoxy, heteroaryl, heteroaryloxy, heterocycloxy, heteroaryl-$C_{1-6}$alkyl, heteroaryl-$C_{1-6}$alkoxy-, heterocyclyl-$C_{1-6}$alkyl-, and heterocyclyl-$C_{1-6}$alkoxy-, wherein heteroaryl is a 5-6 membered ring having one, two, or three heteroatoms each independently selected from N, O, or S, wherein heteroaryl is optionally substituted with one or more substituents each independently selected from $R^b$, wherein heterocyclyl is a 4-7 membered ring optionally substituted by one or more substituents each independently selected from $R^c$, wherein when heterocyclyl contains a —NH— moiety, that —NH— moiety is optionally substituted by $R^d$, wherein $C_{1-6}$alkyl and $C_{1-6}$alkoxy are each independently optionally substituted by one or more groups each independently selected from $R^{p'}$, wherein $C_{2-6}$alkenyl and $C_{2-6}$alkynyl are each independently optionally substituted by one or more substituents each independently selected from $R_p$; wherein $C_{3-6}$cycloalkyl and $C_{3-6}$ cycloalkoxy are each independently optionally substituted by one or more substituents each independently selected from $R^{p''}$;

$R^{B1}$ and $R^{B2}$ are selected, independently for each occurrence, from the group consisting of hydrogen, $C_{1-6}$alkoxy, halogen, $C_{1-6}$alkyl, $C_{2-6}$alkenyl, $C_{3-6}$alkynyl, and $C_{3-6}$cycloalkyl, wherein $C_{2-6}$alkenyl and $C_{3-6}$alkynyl are each independently optionally substituted by one or more groups each independently selected from $R^p$, wherein $C_{1-6}$alkyl and $C_{1-6}$alkoxy are each independently optionally substituted by one or more groups each independently selected from $R^{p'}$, wherein $C_{3-6}$cycloalkyl is optionally substituted by one or more groups each independently selected from $R^{p''}$, or $R^{B1}$ and $R^{B2}$ when taken together with the carbons to which they are attached form a cyclopropyl ring or 4-6 membered ring, wherein the 4-6 membered ring optionally has a group selected from $N(R^h)$, O, or $S(O)_r$ where r is 0, 1, or 2;

$R^a$ and $R^{a'}$ are selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring is optionally substituted by one or more substituents each independently selected from the group consisting of halogen, alkyl, oxo, or hydroxyl;

$R^b$ is selected, independently for each occurrence, from the group consisting of halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-$S(O)_w$— where w is 0, 1, or 2, $C_{1-6}$alkylN$(R^a)$—, $C_{1-6}$alkyl-N$(R^a)$carbonyl, $R^aR^{a'}N$—, $R^aR^{a'}N$-carbonyl-, $R^aR^{a'}N$-carbonyl-$N(R^a)$—; $R^aR^{a'}N$—$SO_2$—, and $C_{1-6}$alkyl-carbonyl-N$(R^a)$—, wherein $C_{2-6}$alkenyl, $C_{3-6}$alkynyl, and $C_{1-6}$alkoxy are each independently optionally substituted by one or more substituents each independently selected from $R^p$; wherein $C_{3-6}$cycloalkyl and $C_{3-6}$cycloalkoxy are each independently optionally substituted by one or more substituents each independently selected from $R^{p''}$, wherein $C_{1-6}$alkyl is optionally substituted by one or more substituents selected from $R^{p'}$;

$R^c$ is selected, independently for each occurrence, from the group consisting of hydroxyl, cyano, oxo, halogen, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-$S(O)_w$— where w is 0, 1, or 2, $C_{1-6}$alkyl-$NR^a$—, $C_{1-6}$alkyl$C_{3-6}$cycloalkyl-, $C_{3-6}$cycloalkyl-$C_{1-6}$alkyl, $R^aR^{a'}N$—, $C_{1-6}$alkylcarbonyl-N$(R^a)$—; $C_{1-6}$alkoxycarbonyl-N$(R^a)$—, $R^aR^{a'}N$—$SO_2$—, $R^aR^{a'}N$-carbonyl-, and $R^aR^{a'}N$-carbonyl-N$(R^a)$, wherein $C_{1-6}$alkyl, $C_{2-6}$alkenyl, $C_{2-6}$alkynyl, $C_{3-6}$cycloalkyl, and $C_{1-6}$alkoxy are each independently optionally substituted by one or more groups each independently selected from $R^t$;

$R^d$ is selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}N$—;

$R^e$ is selected, independently for each occurrence, from the group consisting of hydroxyl, cyano, halogen, oxo, $C_{1-4}$alkyl, $C_{2-4}$alkenyl, $C_{2-4}$alkynyl, $C_{3-6}$cycloalkyl, $C_{1-4}$alkoxy, $C_{3-6}$alkenyloxy, $C_{3-6}$alkynyloxy, $C_{3-6}$cycloalkoxy, $C_{3-6}$cycloalkyl-$C_{1-4}$alkoxy-, $C_{1-4}$alkyl-$S(O)_w$— where w is 0, 1, or 2, $R^aR^{a'}N$—, $R^aR^{a'}N$-carbonyl, $R^aR^{a'}N$-carbonyl-$N(R^a)$—, $R^aR^{a'}N$—$SO_2$—, $C_{1-6}$alkyl-carbonyl-N$(R^a)$—, $C_{1-6}$alkyl-$SO_2$—N$(R^a)$—, $C_{1-6}$alkoxycarbonyl-, and $C_{1-4}$alkoxycarbonyl-N$(R^a)$—, wherein $C_{2-6}$alkenyl, and $C_{2-6}$alkynyl are each independently optionally substituted by one or more substituents each independently selected from $R^p$, wherein $C_{1-6}$alkyl and $C_{1-6}$ alkoxy are each independently optionally substituted by one or more substituents each independently selected from $R^{p'}$, wherein $C_{3-6}$cycloalkyl and $C_{3-6}$cycloalkoxy are each independently optionally substituted by one or more substituents each independently selected from $R^{p''}$;

$R^f$ and $R^g$ are selected, independently for each occurrence, from the group consisting of hydrogen, $C_{1-4}$alkyl optionally substituted by one or more substituents each independently selected from $R^{p'}$, and $C_{3-6}$cycloalkyl optionally substituted by one or more substituents each independently selected from $R^{p''}$, or $R^f$ and $R^g$ when taken together with the nitrogen to which they are attached form a 4-7 membered heterocyclyl optionally substituted by one or more substituents each independently selected from the group consisting of halogen, hydroxyl, oxo, cyano, $C_{1-6}$alkyl, $C_{1-6}$alkoxy, $R^aR^{a'}N-$, $C_{1-6}$alkylcarbonyl-$N(R^a)-$, $C_{1-6}$alkoxycarbonyl-$N(R^a)-$, $R^aR^{a'}N-SO_2-$, $R^aR^{a'}N$-carbonyl-, and $R^aR^{a'}N$-carbonyl-$N(R^a)$, wherein $C_{1-6}$alkyl and $C_{1-4}$alkoxy are each independently optionally substituted by one or more substituents each independently selected from the group consisting of $R^aR^{a'}N-$, halogen, hydroxy, cyano, $C_{1-4}$alkoxycarbonyl, $R^aR^{a'}N$-carbonyl, $R^aR^{a'}N-SO_2-$, $C_{1-4}$alkoxy, and $C_{1-4}$alkylS$(O)_w-$ where w is 0, 1, or 2;

$R^p$ is selected, independently for each occurrence, from the group consisting of $R^aR^{a'}N-$, halogen, hydroxy, cyano, $C_{1-4}$alkoxycarbonyl, $R^aR^{a'}N$-carbonyl, $R^aR^{a'}N-SO_2-$, $C_{1-4}$alkoxy, and $C_{1-4}$alkylS$(O)_w-$ where w is 0, 1, or 2;

$R^{p'}$ is selected, independently for each occurrence, from the group consisting of $R^aR^{a'}N-$, halogen, hydroxy, cyano, $C_{1-4}$alkoxycarbonyl, $R^aR^{a'}N$-carbonyl, $R^aR^{a'}N-SO_2-$, $C_{1-4}$alkoxy, $C_{1-4}$alkylS$(O)_w-$ where w is 0, 1, or 2, and $C_{3-6}$cycloalkyl, wherein $C_{3-6}$cycloalkyl is optionally substituted by one or more substituents each independently selected from $R^{p''}$;

$R^{p''}$ is selected, independently for each occurrence, from the group consisting of $R^aR^{a'}N-$, halogen, hydroxy, cyano, $C_{1-4}$alkoxycarbonyl, $R^aR^{a'}N$-carbonyl, $R^aR^{a'}N-SO_2-$, $C_{1-4}$alkoxy, $C_{1-4}$alkylS$(O)_w$ where w is 0, 1, or 2, and $C_{1-6}$alkyl, wherein $C_{1-6}$ alkyl is optionally substituted by one or more substituents each independently selected from $R^p$;

$R^r$ is selected, independently for each occurrence, from the group consisting of $R^fR^gN-$, halogen, cyano, hydroxyl, and $C_{1-6}$alkoxy;

$R^h$ is selected, independently for each occurrence, from the group consisting of hydrogen; $C_{1-6}$alkyl, $C_{3-6}$alkenyl and $C_{3-6}$alkynyl, wherein none of the carbon atoms forming an unsaturated bond are bonded to N; $C_{3-6}$cycloalkyl; $C_{1-6}$alkyl-$S(O)_2-$; and $C_{1-6}$alkyl-$N(R^a)$carbonyl; wherein $C_{1-6}$alkyl is optionally substituted by one or more substituents each independently selected from $R^{p'}$; wherein $C_{3-6}$alkenyl and $C_{3-6}$alkynyl are each independently optionally substituted by one or more substituents each independently selected from $R^p$; wherein $C_{3-6}$cycloalkyl is optionally substituted by one or more substituents each independently selected from $R^{p''}$.

DETAILED DESCRIPTION

The features and other details of the disclosure will now be more particularly described. Before further description, certain terms employed in the specification, examples, and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkyoxycarbonyl" as used herein refers to a straight or branched alkyl group attached to oxygen, attached to a carbonyl group (alkyl-O—C(O)—). Exemplary alkoxycarbonyl groups include, but are not limited to, alkoxycarbonyl groups of 1-6 carbon atoms, referred to herein as $C_{1-6}$alkoxycarbonyl. Exemplary alkoxycarbonyl groups include, but are not limited to, methoxycarbonyl, ethoxycarbonyl, t-butoxycarbonyl, etc.

The term "alkenyloxy" used herein refers to a straight or branched alkenyl group attached to an oxygen (alkenyl-O). Exemplary alkenoxy groups include, but are not limited to, groups with an alkenyl group of 3-6 carbon atoms referred to herein as $C_{3-6}$alkenyloxy. Exemplary "alkenyloxy" groups include, but are not limited to allyloxy, butenyloxy, etc.

The term "alkynyloxy" used herein refers to a straight or branched alkynyl group attached to an oxygen (alkynyl-O)). Exemplary alkynyloxy groups include, but are not limited to, propynyloxy.

The term "alkyl" as used herein refers to a saturated straight or branched hydrocarbon, such as a straight or branched group of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkylcarbonyl" as used herein refers to a straight or branched alkyl group attached to a carbonyl group (alkyl-C(O)—). Exemplary alkylcarbonyl groups include, but are not limited to, alkylcarbonyl groups of 1-6 atoms, referred to herein as $C_{1-6}$alkylcarbonyl groups. Exemplary alkylcarbonyl groups include, but are not limited to, acetyl, propanoyl, isopropanoyl, butanoyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The term "carbonyl" as used herein refers to the radical —C(O)—.

The term "cyano" as used herein refers to the radical —CN.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of for example 3-6, or 4-6 carbons, referred to herein, e.g., as $C_{3-6}$cycloalkyl or $C_{4-6}$cycloalkyl and derived from a cycloalkane. Exemplary cycloalkyl groups include, but are not limited to, cyclohexyl, cyclohexenyl, cyclopentyl, cyclobutyl or, cyclopropyl.

The terms "halo" or "halogen" as used herein refer to F, Cl, Br, or I.

The terms "heteroaryl" or "heteroaromatic group" as used herein refers to a monocyclic aromatic 4-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridyl, and pyrimidinyl.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. A heterocycle may be fused to one or more phenyl, partially unsaturated, or saturated rings. Examples of heterocyclyl groups include but are not limited to pyrrolidine, piperidine, morpholine, thiomorpholine, and piperazine.

The term "heterocyclylalkoxy" as used herein refers to a heterocyclyl-alkyl-O— group.

The term "heterocyclyloxyalkyl" refers to a heterocyclyl-O-alkyl- group.

The term "heterocyclyloxy" refers to a heterocyclyl-O— group.

The term "heteroaryloxy" refers to a heteroaryl-O— group.

The terms "hydroxy" and "hydroxyl" as used herein refers to the radical —OH.

The term "oxo" as used herein refers to the radical =O.

"Pharmaceutically or pharmacologically acceptable" include molecular entities and compositions that do not produce an adverse, allergic, or other untoward reaction when administered to an animal, or a human, as appropriate. For human administration, preparations should meet sterility, pyrogenicity, general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated is desirably a mammal in which treatment of obesity, or weight loss is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal, or human that is being sought by the researcher, veterinarian, medical doctor, or other clinician. The compounds are administered in therapeutically effective amounts to treat a disease. Alternatively, a therapeutically effective amount of a compound is the quantity required to achieve a desired therapeutic and/or prophylactic effect, such as an amount which results in weight loss.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion, or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. Various stereoisomers of these compounds and mixtures thereof are encompassed by this disclosure. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomers and diastereomers may be designated by the symbols "(+)," "(−)." "R" or "S," depending on the configuration of substituents around the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds. The symbol ⎓ denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. Various stereoisomers of these compounds and mixtures thereof are encompassed by this disclosure.

Individual enantiomers and diasteriomers of the compounds can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using steroselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like. In one embodiment, the compound is amorphous. In one embodiment, the compound is a polymorph. In another embodiment, the compound is in a crystalline form.

Also embraced are isotopically labeled compounds which are identical to those recited herein, except that one or more atoms are replaced by an atom having an atomic mass or mass number different from the atomic mass or mass number usually found in nature. Examples of isotopes that can be incorporated into the compounds include isotopes of hydrogen, carbon, nitrogen, oxygen, phosphorus, sulfur, fluorine and chlorine, such as $^{2}H$, $^{3}H$, $^{13}C$, $^{14}C$, $^{15}N$, $^{18}O$, $^{17}O$, $^{32}P$, $^{35}S$, $^{18}F$, and $^{36}Cl$, respectively. For example, a compound may have one or more H atom replaced with deuterium.

Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labeled compounds can generally be prepared by following procedures analogous to those disclosed in the Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and or reductive metabolism) in various locations (such as in the intestinal lumen or upon transit of the intestine, blood, or liver). Prodrugs are well known in the art (for example, see Rautio, Kumpulainen, et al, Nature Reviews Drug Discovery 2008, 7, 255). For example, if a compound or a pharmaceutically acceptable salt, hydrate, or solvate of the compound contains a carboxylic acid functional group, a prodrug can comprise an ester formed by the replacement of the hydrogen atom of the acid group with a group such as $(C_{1-8})$alkyl, $(C_{2-12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_{1-2})$alkylamino$(C_{2-3})$alkyl (such as β-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino$(C_{2-3})$alkyl.

Similarly, if a compound contains an alcohol functional group, a prodrug can be formed by the replacement of the hydrogen atom of the alcohol group with a group such as $(C_{1-6})$alkanoyloxymethyl, 1-(($C_{1-6}$)alkanoyloxy)ethyl, 1-methyl-1-(($C_{1-6}$)alkanoyloxy)ethyl $(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_{1-6})$alkyl$)_2$ or glycosyl (the radical resulting from the removal of a hydroxyl group of the hemiacetal form of a carbohydrate).

If a compound incorporates an amine functional group, a prodrug can be formed, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can be metabolically cleaved to generate a bioactive primary or secondary amine. For examples, see Simplício, et al., *Molecules* 2008, 13, 519 and references therein.

I. Tetrazole Compounds

In certain embodiments, compounds of formula I are provided:

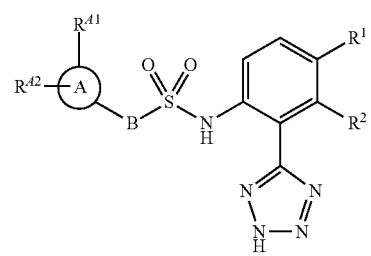

I and pharmaceutically acceptable salts, stereoisomers, esters, and prodrugs thereof, wherein:

A may be a ring selected from the group consisting of phenyl, heteroaryl, $C_{3-6}$cycloalkyl, and heterocyclyl, wherein for example, heteroaryl is a 5-6 membered ring having one, two, or three heteroatoms each independently selected from N, O, or S, and wherein heterocyclyl may be, for example, a 4-7 membered ring;

B may be selected from the group consisting of a bond or $(CR^{B1}R^{B2})$;

$R^1$ may be selected from the group consisting of hydrogen, halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— where w is 0, 1, or 2, heteroaryl, heterocyclyl, heterocyclyloxy, heterocyclyl-$C_{1-6}$alkyl, and heterocyclyl-$C_{1-6}$alkoxy, wherein heteroaryl is a 5-6 membered ring having one, two, or three heteroatoms each independently selected from N, O, or S, wherein heteroaryl is optionally substituted with one or more substituents each independently selected from $R^b$, wherein heterocyclyl is a 4-7 membered ring optionally substituted by one or more substituents each independently selected from $R^c$, and wherein when heterocyclyl contains a —NH— moiety, that —NH— moiety is optionally substituted by $R^d$, wherein $C_{2-6}$alkenyl, $C_{2-6}$alkynyl, $C_{3-6}$alkenyloxy, and $C_{3-6}$alkynyloxy are each independently optionally substituted by one or more substituents each independently selected from $R^p$, wherein $C_{1-6}$alkyl and $C_{1-6}$alkoxy are each independently optionally substituted by one or more substituents each independently selected from $R^{p'}$, wherein $C_{3-6}$cycloalkyl and $C_{3-6}$cycloalkoxy are each independently optionally substituted by one or more substituents each independently selected from $R^{p''}$;

$R^2$ may be selected from the group consisting of halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkyloxy, $C_{1-6}$alkyl-S(O)$_2$—, $C_{3-6}$cycloalkyl-$C_{1-4}$alkyl-, $C_{3-6}$cycloalkyl-$C_{1-4}$alkoxy-, phenyl-$C_{1-6}$alkyl-, phenyl, phenoxy, phenyl-$C_{1-6}$alkoxy-, heteroaryl, heteroaryloxy, heteroaryl-$C_{1-6}$alkyl, heteroaryl-$C_{1-6}$alkoxy, heterocyclyl-$C_{1-6}$alkyl-, and heterocyclyl-$C_{1-6}$alkoxy-, wherein heteroaryl is a 5-6 membered ring having one, two, or three heteroatoms each independently selected from N, O, or S, wherein heteroaryl and phenyl group are each independently optionally substituted with one or more substituents each independently selected from $R^b$, wherein heterocyclyl is a 4-7 membered ring optionally substituted by one or more substituents each independently selected from $R^c$, and wherein when heterocyclyl contains a —NH— moiety, that —NH— moiety is optionally substituted by $R^d$, wherein $C_{1-6}$alkyl, $C_{2-6}$alkenyl, $C_{2-6}$alkynyl, $C_{1-6}$alkoxy, $C_{3-6}$alkenyloxy, and $C_{3-6}$alkynyloxy are each independently optionally substituted by one or more substituents each independently selected from halogen, hydroxyl, $R^aR^{a'}N$—, and cyano, wherein $C_{3-6}$cycloalkyl, and $C_{3-6}$cycloalkoxy are each independently optionally substituted by one or more substituents each independently selected from halogen, hydroxyl, $R^aR^{a'}N$—, cyano, and $C_{1-6}$alkyl; or $R^1$ and $R^2$ when taken together with the carbons to which they are attached may form a 5-7 membered saturated, partially unsaturated, or unsaturated ring, optionally having 1, 2, or 3 groups each independently selected from O, $NR^h$, and S(O)$_r$ where r is 0, 1, or 2, wherein the 5-7 membered ring is optionally substituted on a carbon by one or more groups each independently selected from $R^e$;

$R^{A1}$ is selected, independently for each occurrence, from the group consisting of hydrogen, hydroxyl, cyano, halogen, $C_{1-6}$alkyl, $C_{2-6}$alkenyl, $C_{3-6}$alkynyl, $C_{3-6}$cycloalkyl, $C_{1-6}$alkoxy, and $R^fR^gN$—, wherein $C_{1-6}$alkyl, $C_{2-6}$alkenyl, $C_{3-6}$ alkynyl, $C_{3-6}$cycloalkyl, and $C_{1-6}$alkoxy are each independently optionally substituted with one or more halogens;

$R^{A2}$ may be selected, independently for each occurrence, from the group consisting of hydrogen, hydroxyl, cyano, halogen, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— where w is 0, 1, or 2, $R^fR^gN$—, $R^fR^gN$-carbonyl-, $R^fR^gN$-carbonyl-N($R^a$)—, $R^fR^gN$—SO$_2$—, $C_{1-6}$alkyl-carbonyl-N($R^a$)—, $C_{1-6}$ alkylsulfonylN($R^a$)—, $C_{1-6}$alkoxycarbonyl-N($R^a$)—, phenyl, phenoxy, phenyl-$C_{1-6}$alkyl-, phenyl-$C_{1-6}$alkoxy, heteroaryl, heteroaryloxy, heterocycloxy, heteroaryl-$C_{1-6}$alkyl, heteroaryl-$C_{1-6}$alkoxy-, heterocyclyl-$C_{1-6}$alkyl-, and heterocyclyl-$C_{1-6}$alkoxy-, wherein heteroaryl is a 5-6 membered ring having one, two, or three heteroatoms each independently selected from N, O, or S, wherein heteroaryl is optionally substituted with one or more substituents each independently selected from $R^b$, wherein heterocyclyl is a 4-7 membered ring optionally substituted by one or more substituents each independently selected from $R^c$, and wherein when heterocyclyl contains a —NH— moiety, that —NH— moiety is optionally substituted by $R^d$, wherein $C_{1-6}$alkyl and $C_{1-6}$alkoxy are each independently optionally substituted by one or more groups each independently selected from $R^{p'}$, wherein $C_{2-6}$alkenyl and $C_{2-6}$ alkynyl are independently optionally substituted by one or more substituents each independently selected from $R^p$; wherein $C_{3-6}$cycloalkyl and $C_{3-6}$ cycloalkoxy are each independently optionally substituted by one or more substituents each independently selected from $R^{p''}$;

$R^{B1}$ and $R^{B2}$ may be selected, independently for each occurrence, from the group consisting of hydrogen, $C_{1-6}$alkoxy, halogen, $C_{1-6}$alkyl, $C_{2-6}$alkenyl, $C_{3-6}$alkynyl, and $C_{3-6}$cycloalkyl, wherein $C_{2-6}$alkenyl and $C_{3-6}$alkynyl are each independently optionally substituted by one or more groups each independently selected from $R^p$, wherein $C_{1-6}$alkyl and $C_{1-6}$alkoxy are each independently optionally substituted by one or more groups each independently selected from $R^{p'}$, wherein $C_{3-6}$cycloalkyl is optionally substituted by one or more groups each independently selected from $R^{p'}$, or $R^{B1}$ and $R^{B2}$ when taken together with the carbons to which they are attached form a cyclopropyl ring or 4-6 membered ring, wherein the 4-6 membered ring optionally has a group selected from N($R^h$), O, or S(O)$_r$ where r is 0, 1, or 2;

$R^a$ and $R^{a'}$ may be selected, independently for each occurrence, from the group consisting of hydrogen and $C_{1-6}$alkyl, or $R^a$ and $R^{a'}$ when taken together with the nitrogen to which they are attached form a 4-6 membered heterocyclic ring, wherein $C_{1-6}$alkyl is optionally substituted by one or more substituents each independently selected from the group consisting of halogen, oxo, and hydroxyl, and wherein the heterocyclic ring may be optionally substituted by one or more substituents each independently selected from the group consisting of halogen, alkyl, oxo, or hydroxyl;

$R^b$ may be selected, independently for each occurrence, from the group consisting of halogen, hydroxyl, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$alkynyloxy, $C_{3-6}$cycloalkoxy, $C_{1-6}$alkyl-S(O)$_w$— where w is 0, 1, or 2, $C_{1-6}$alkylN($R^a$)—, $C_{1-6}$alkyl-N($R^a$)carbonyl, $R^aR^{a'}N$—, $R^aR^{a'}N$-carbonyl-, $R^aR^{a'}N$-carbonyl-N($R^a$)—; $R^aR^{a'}N$—SO$_2$—, and $C_{1-6}$alkyl-carbonyl-N($R^a$)—, wherein $C_{2-6}$alkenyl, $C_{3-6}$alkynyl, and $C_{1-6}$alkoxy are each independently optionally substituted by one or more substituents each independently selected from $R^p$; wherein $C_{3-6}$cycloalkyl and $C_{3-6}$cycloalkoxy are each independently optionally substituted by one or more substituents each independently selected from $R^{p"}$, wherein $C_{1-6}$alkyl is optionally substituted by one or more substituents selected from $R^{p'}$;

$R^c$ may be selected, independently for each occurrence, from the group consisting of hydroxyl, cyano, oxo, halogen, $C_{1-6}$alkyl, $C_{2-6}$alkenyl, $C_{2-6}$alkynyl, $C_{3-6}$cycloalkyl, $C_{1-6}$alkoxy, $C_{1-6}$alkyl-S(O)$_w$— where w is 0, 1, or 2, $C_{1-6}$alkyl-NR$^a$—, $C_{1-6}$alkylC$_{3-6}$cycloalkyl-, $C_{3-6}$cycloalkyl-$C_{1-6}$alkyl, $R^aR^{a'}$N—, $C_{1-6}$alkylcarbonyl-N(R$^a$)—; $C_{1-6}$alkoxycarbonyl-N(R$^a$)—, $R^aR^{a'}$N—SO$_2$—, $R^aR^{a'}$N-carbonyl-, and $R^aR^{a'}$N-carbonyl-N(R$^a$), wherein $C_{1-6}$alkyl, $C_{2-6}$alkenyl, $C_{2-6}$alkynyl, $C_{3-6}$cycloalkyl, and $C_{1-6}$alkoxy are each independently optionally substituted by one or more groups each independently selected from R$^t$;

$R^d$ may be selected, independently for each occurrence, from the group consisting of $C_{1-6}$alkyl, $C_{1-6}$alkylcarbonyl, and $C_{1-6}$alkylsulfonyl, wherein $C_{1-6}$alkyl is optionally substituted by one or more substituents each independently selected from halogen, hydroxyl, and $R^aR^{a'}$N—;

$R^e$ may be selected, independently for each occurrence, from the group consisting of hydroxyl, cyano, halogen, oxo, $C_{1-4}$alkyl, $C_{2-4}$alkenyl, $C_{2-4}$alkynyl, $C_{3-6}$cycloalkyl, $C_{1-4}$alkoxy, $C_{3-6}$alkenyloxy, $C_{3-6}$alkynyloxy, $C_{3-6}$cycloalkoxy, $C_{3-6}$cycloalkyl-$C_{1-4}$alkoxy-, $C_{1-4}$alkyl-S(O)$_w$— where w is 0, 1, or 2, $R^aR^{a'}$N—, $R^aR^{a'}$N-carbonyl, $R^aR^{a'}$N-carbonyl-N(R$^a$)—, $R^aR^{a'}$N—SO$_2$—, $C_{1-6}$alkyl-carbonyl-N(R$^a$)—, $C_{1-6}$alkyl-SO$_2$—N(R$^a$)—, $C_{1-6}$alkoxycarbonyl-, and $C_{1-4}$alkoxycarbonyl-N(R$^a$)—, wherein $C_{2-6}$alkenyl, and $C_{2-6}$alkynyl are each independently optionally substituted by one or more substituents each independently selected from $R^p$, wherein $C_{1-6}$alkyl and $C_{1-6}$ alkoxy are each independently optionally substituted by one or more substituents each independently selected from $R^{p'}$, wherein $C_{3-6}$cycloalkyl and $C_{3-6}$cycloalkoxy are each independently optionally substituted by one or more substituents each independently selected from $R^{p"}$;

$R^f$ and $R^g$ may be selected, independently for each occurrence, from the group consisting of hydrogen, $C_{1-4}$alkyl optionally substituted by one or more substituents each independently selected from $R^{p'}$, and $C_{3-6}$cycloalkyl optionally substituted by one or more substituents each independently selected from $R^{p"}$, or $R^f$ and $R^g$ when taken together with the nitrogen to which they are attached form a 4-7 membered heterocyclyl optionally substituted by one or more substituents each independently selected from the group consisting of halogen, hydroxyl, oxo, cyano, $C_{1-6}$alkyl, $C_{1-6}$alkoxy, $R^aR^{a'}$N—, $C_{1-6}$alkylcarbonyl-N(R$^a$)—, $C_{1-6}$alkoxycarbonyl-N(R$^a$)—, $R^aR^{a'}$N—SO$_2$—, $R^aR^{a'}$N-carbonyl-, and $R^aR^{a'}$N-carbonyl-N(R$^a$), wherein $C_{1-6}$alkyl and $C_{1-4}$alkoxy are each independently optionally substituted by one or more substituents each independently selected from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, and $C_{1-4}$alkylS(O)$_w$— where w is 0, 1, or 2;

$R^p$ may be selected, independently for each occurrence, from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, and $C_{1-4}$alkylS(O)$_w$— where w is 0, 1, or 2;

$R^{p'}$ may be selected, independently for each occurrence, from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, $C_{1-4}$alkylS(O)$_w$— where w is 0, 1, or 2, and $C_{3-6}$cycloalkyl, wherein $C_{3-6}$cycloalkyl is optionally substituted by one or more substituents each independently selected from $R^{p"}$;

$R^{p"}$ may be selected, independently for each occurrence, from the group consisting of $R^aR^{a'}$N—, halogen, hydroxy, cyano, $C_{1-4}$alkoxycarbonyl, $R^aR^{a'}$N-carbonyl, $R^aR^{a'}$N—SO$_2$—, $C_{1-4}$alkoxy, $C_{1-4}$alkylS(O)$_w$ where w is 0, 1, or 2, and $C_{1-6}$alkyl, wherein $C_{1-6}$alkyl is optionally substituted by one or more substituents each independently selected from $R^p$;

$R^t$ may be selected, independently for each occurrence, from the group consisting of $R^fR^gN$—, halogen, cyano, hydroxyl, and $C_{1-6}$alkoxy;

$R^h$ may be selected, independently for each occurrence, from the group consisting of hydrogen; $C_{1-6}$alkyl, $C_{3-6}$alkenyl and $C_{3-6}$alkynyl, wherein none of the carbon atoms forming an unsaturated bond are bonded to N; $C_{3-6}$cycloalkyl; $C_{1-6}$alkyl-S(O)$_2$—; and $C_{1-6}$alkyl-N(R$^a$)carbonyl; wherein $C_{1-6}$alkyl is optionally substituted by one or more substituents each independently selected from $R^{p'}$; wherein $C_{3-6}$alkenyl and $C_{3-6}$alkynyl are each independently optionally substituted by one or more substituents each independently selected from $R^p$; wherein $C_{3-6}$cycloalkyl is optionally substituted by one or more substituents each independently selected from $R^{p"}$.

In some embodiments, A may be phenyl.

In some embodiments, B may be a bond.

In certain embodiments, $R^1$ may be selected from the group consisting of hydrogen, halogen, cyano, hydroxyl, $C_{1-3}$alkyl, $C_{2-4}$alkenyl, $C_{2-4}$alkynyl, $C_{3-6}$cycloalkyl, $C_{1-4}$alkoxy, $C_{3-4}$alkenyloxy, and $C_{3-4}$alkynyloxy, wherein $C_{2-4}$alkenyl, $C_{2-4}$alkynyl, $C_{3-4}$alkenyloxy, and $C_{3-4}$alkynyloxy are each independently optionally substituted by one or more substituents each independently selected from $R^p$, wherein $C_{1-3}$alkyl and $C_{1-4}$alkoxy are each independently optionally substituted by one or more substituents each independently selected from $R^{p'}$, wherein $C_{3-6}$cycloalkyl is optionally substituted by one or more substituents each independently selected from $R^{p"}$.

In other embodiments, $R^1$ may be selected from the group consisting of H or $C_{1-3}$ alkyl.

In yet other embodiments, $R^1$ may be H.

In some embodiments, $R^2$ may be selected from the group consisting of halogen, cyano, $C_{1-6}$alkyl, $C_{2-6}$alkenyl, $C_{2-6}$alkynyl, $C_{3-6}$cycloalkyl, $C_{1-6}$alkoxy, $C_{3-6}$alkenyloxy, $C_{3-6}$ alkynyloxy, $C_{3-6}$cycloalkyloxy, $C_{1-6}$alkyl-S(O)$_2$—, $C_{3-6}$cycloalkyl-$C_{1-4}$alkyl-, and $C_{3-6}$cycloalkyl-$C_{1-4}$alkoxy-, wherein $C_{1-6}$alkyl, $C_{2-6}$alkenyl, $C_{2-6}$alkynyl, $C_{1-6}$alkoxy, $C_{3-6}$alkenyloxy, and $C_{3-6}$alkynyloxy are each independently optionally substituted by one or more substituents each independently selected from halogen, hydroxyl, $R^aR^{a'}$N—, or cyano, wherein $C_{3-6}$cycloalkyl and $C_{3-6}$cycloalkoxy are each independently optionally substituted by one or more substituents each independently selected from halogen, hydroxyl, $R^aR^{a'}$N—, cyano, and $C_{1-6}$alkyl.

In other embodiments, $R^2$ is selected from the group consisting of halogen, cyano, $C_{1-6}$alkyl, $C_{3-6}$cycloalkyl, $C_{1-6}$alkoxy, $C_{3-6}$cycloalkyloxy, $C_{3-6}$cycloalkyl-$C_{1-4}$alkyl-, and $C_{3-6}$cycloalkyl-$C_{1-4}$alkoxy-, and $C_{1-6}$alkoxy-$C_{1-6}$alkyl-.

In still other embodiments, $R^2$ may be selected from the group consisting of bromine, methyl, methoxy, or cyclopropyl.

In some embodiments, $R_1$ and $R_2$ when taken together with the ring to which they are attached may form:

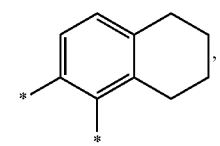

where * represents the points of attachment in Formula I.

In some embodiments, $R^{A1}$ may be selected from the group consisting of hydrogen, halogen, $C_{1-6}$alkyl, or $C_{1-6}$alkoxy, wherein $C_{1-6}$alkyl and $C_{1-6}$alkoxy are each independently optionally substituted with one or more halogens.

In other embodiments, $R^{A1}$ may be hydrogen.

In some embodiments, $R^{A2}$ may be selected from the group consisting of hydrogen, halogen, $C_{1-6}$alkyl, $C_{2-6}$alkenyl, $C_{3-6}$cycloalkyl, $C_{1-6}$alkoxy, and $C_{3-6}$alkenyloxy, wherein $C_{1-6}$alkyl and $C_{1-6}$alkoxy are each independently optionally substituted by one or more substituents each independently selected from $R^{P'}$, wherein $C_{2-6}$alkenyl is optionally substituted by one or more substituents each independently selected from $R^{P}$, wherein $C_{3-6}$cycloalkyl is optionally substituted by one or more substituents each independently selected from $R^{P''}$.

In certain embodiments, $R^{B1}$ and $R^{B2}$ may be H.

Provided herein are compounds that may be selected from the group consisting of N-[1-(1H-tetrazol-5-yl)-5,6,7,8-tetrahydronaphthalen-2-yl]-benzenesulfonamide, N-[3-cyclopropyl-2-(1H-tetrazol-5-yl)-phenyl]-benzenesulfonamide, N-[3-methoxy-2-(1H-tetrazol-5-yl)-phenyl]-benzenesulfonamide, N-[3-methyl-2-(1H-tetrazol-5-yl)-phenyl]-benzenesulfonamide, N-[3-bromo-2-(1H-tetrazol-5-yl)-phenyl]-benzenesulfonamide and pharmaceutically acceptable salts thereof and stereoisomers thereof.

Procedures for making compounds described herein are provided below with reference to Schemes 1 and 2. In the reactions described below, it may be necessary to protect reactive functional groups (such as hydroxy, amino, thio, or carboxy groups) to avoid their unwanted participation in the reactions. The incorporation of such groups, and the methods required to introduce and remove them are known to those skilled in the art. (For example, see Greene, Wuts, *Protective Groups in Organic Synthesis*. 2nd Ed. (1999)). The deprotection step may be the final step in the synthesis such that the removal of protecting groups affords a compound of Formula I, as disclosed herein, or as exemplified in, for example, General Formula I, below. Starting materials used in the following schemes can be purchased or prepared by methods described in the chemical literature, or by adaptations thereof, using methods known by those skilled in the art. The order in which the steps are performed can vary depending on the groups introduced and the reagents used, but would be apparent to those skilled in the art.

Compounds of General Formula I may be prepared according to Scheme 1. Specific steps in the synthetic process are described in more detail below.

SCHEME 1

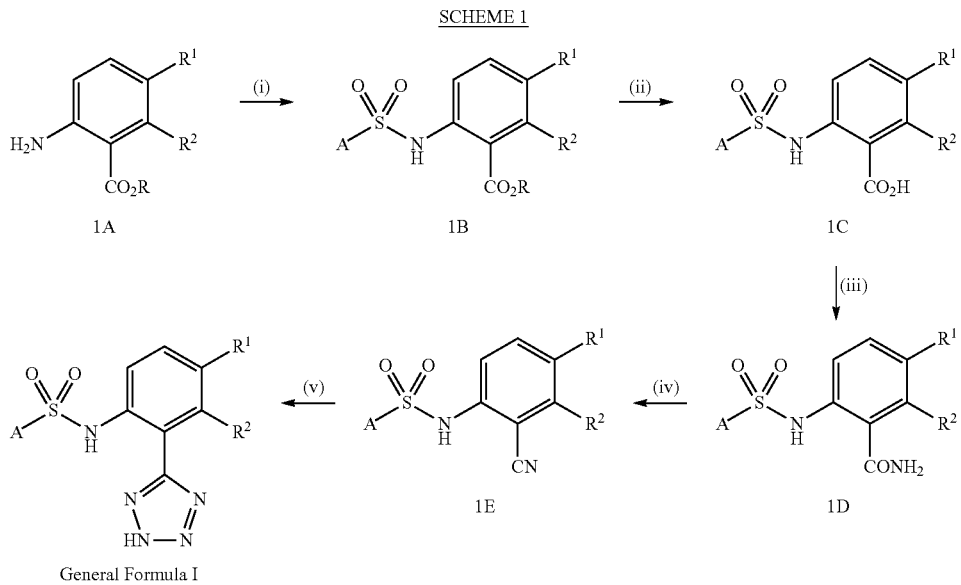

In Scheme 1, Step (i), an anthranilate ester 1A may be converted to a sulfonamide 1B by treatment with an appropriate sulfonyl chloride in the presence of a base (such as pyridine, triethylamine, or di-isopropylethylamine) optionally in a solvent (such as dichloromethane, dimethylformamide, or N-methylpyrrolidinone) at a temperature between room temperature and the reflux temperature of the solvent.

In Scheme 1, Step (ii), a sulfonamide ester 1B may be converted to the corresponding carboxylic acid 1C. Depending on the nature of the ester this may be achieved in a number of ways. For example a methyl, ethyl or benzyl ester may be treated with an aqueous base (such as sodium hydroxide or lithium hydroxide) in a solvent (such as an alcohol solvent, for example, methanol or ethanol, or an ether solvent, for example, dioxane or tetrahydrofuran) at a temperature between room temperature and the reflux temperature of the solvent or by irradiating in the microwave at a temperature between 120° C. and 160° C. for a period from between 10 minutes and 2 hours. If the ester 1B is, for example, a tertiary butyl ester, the conversion to the carboxylic acid may be achieved by the treatment with an acid in an appropriate solvent (for example trifluoroacetic acid) optionally in a chlorinated solvent (such as dichloromethane) or a solution of hydrogen chloride in a solvent (such as dioxane). If the ester is a benzyl ester, the conversion to the carboxylic acid may be achieved by catalytic hydrogenation, in the presence of a metal catalyst (such as palladium or palladium hydroxide on a solid support, for example carbon) in a solvent (such as dioxane or ethyl acetate).

In Scheme 1, Step (iii), a carboxylic acid 1C may be converted to the corresponding primary amide 1D. For example, the carboxylic acid may be converted to the acid chloride by the treatment of the carboxylic acid with a chlorinating agent (such as oxalyl chloride or thionyl chloride) optionally in the presence of a catalyst (such as N,N-dimethylformamide) optionally in a solvent (such as dichloromethane or toluene) at a temperature between room temperature and the reflux temperature of the solvent. The acid chloride may then be treated with ammonia (gas or solution) in a solvent (such as water or tetrahydrofuran) to give the amide.

Alternatively, in Scheme 1, Step (iii), the carboxylic acid may be treated with a coupling agent (such as 2-(7-aza-1H-benzotriazole-1-yl)-1,1,3,3-tetramethyluronium hexafluorophosphate, dicyclohexylcarbonyldiimide, carbonyl-diimidazole, or other similar coupling agent) in the presence of ammonia or a source of ammonia, such as an ammonium salt (for example ammonium chloride) in a solvent (such as dichloromethane or N,N-dimethylformamide) at a temperature between room temperature and the reflux temperature of the solvent. A wide range of conditions are known to one skilled in the art for the conversion of a carboxylic acid to a primary amide.

Alternatively, in Scheme 1, Step (v), the nitrile may be treated with a silyl azide (such as trimethylsilyl azide) optionally in the presence of an organotin reagent (such as an alkyl tin oxide, for example di-butyl tin oxide) in a solvent (such as 1,2-dichloroethane) at a temperature between room temperature and the reflux temperature of the solvent or alternatively by irradiation in a microwave at a temperature between 120° C. and 180° C.

Alternatively, in Scheme 1, Step (v), the nitrile may be treated with an organotin azide (such as tributyltin azide) in a solvent (such as 1,2-dichlorobenzene) at a temperature from room temperature to the reflux temperature of the solvent or alternatively by irradiation in the microwave at a temperature between 120° C. and 180° C. A wide range of conditions are known to one skilled in the art for the conversion of a nitrile to a tetrazole.

Alternatively, compounds of General Formula I may also be prepared according to Scheme 2.

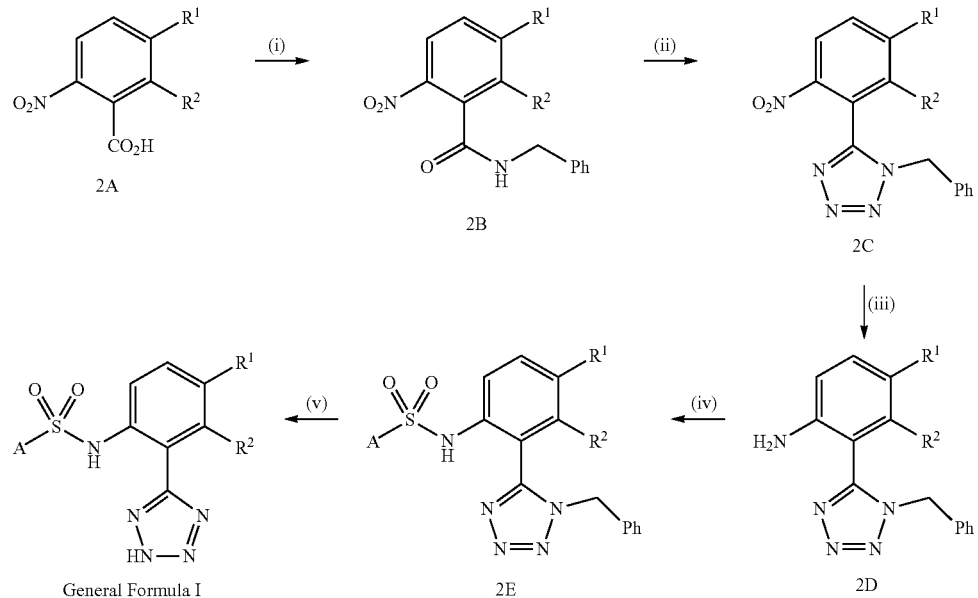

SCHEME 2

In Scheme 1, Step (iv), a primary amide 1D may be converted to the nitrile 1E. This may be achieved by dehydration of the amide. For example, the primary amide may be treated with a dehydrating reagent (such as thionyl chloride, phosphorus oxychloride, or phosphorus pentachloride) optionally in a solvent (such as 1,2-dichloroethane, chlorobenzene, toluene, or dimethylformamide) at a temperature between room temperature and the reflux temperature of the solvent. A wide range of conditions are known to one skilled in the art for the conversion of a primary amide to a nitrile.

In Scheme 1, Step (v), a nitrile 1E may be converted to a tetrazole of General Formula I. This may be achieved by treatment of the nitrile with an azide. For example, the nitrile may be treated with sodium azide in the presence of an organotin halide (such as tributyltin chloride), optionally in the presence of an ammonium salt (such as tetrabutylammonium bromide) in a solvent (such as N,N-dimethylformamide) at a temperature between room temperature and the reflux temperature of the solvent or alternatively by irradiation in a microwave at a temperature between 160° C. and 230° C.

In Scheme 2, Step (i), a nitrobenzoic acid 2A is converted to the N-phenylamide 2B. For example, the carboxylic acid may be converted to the acid chloride by treatment of the carboxylic acid with a chlorinating agent (such as oxalyl chloride or thionyl chloride) optionally in the presence of a catalyst (such as N,N-dimethylformamide) optionally in a solvent (such as dichloromethane or toluene) at a temperature between room temperature and the reflux temperature of the solvent. The acid chloride may then be treated with benzylamine in a solvent (such as dichloromethane or tetrahydrofuran) to give the amide.

Alternatively, in Scheme 2, Step (i), the carboxylic acid may be treated with a coupling agent (for example, 2-(7-aza-1H-benzotriazole-1-yl)-1,1,3,3-tetramethyluronium hexafluorophosphate, dicyclohexylcarbonyldiimide, carbonyl-diimidazole, or other similar coupling agent) in the presence of benzylamine in a solvent (such as dichloromethane or N,N-dimethylformamide) at a temperature between room temperature and the reflux temperature of the solvent. A wide range of conditions are known to one skilled in the art for the conversion of a carboxylic acid to a secondary amide.

In Scheme 2, Step (ii), an N-benzylamide 2B is converted to an N-benzyltetrazole 2C. This may be achieved by the treatment of the amide with a chlorinating agent (such as phosphorus pentachloride) in a solvent (such as dichloromethane) followed by treatment of the intermediate generated with an azide (such as trimethylsilyl azide) at a temperature between 0° C. and the reflux temperature of the solvent (preferably at room temperature).

In Scheme 2, Step (iii), the nitro intermediate 2C is converted to the aniline 2D. This may be achieved by treating a solution of the nitro intermediate in a solvent (such as methanol, ethanol, or ethyl acetate) with a hydrogenation catalyst (such as palladium on carbon, palladium hydroxide on carbon, or platinum on carbon) under an atmosphere of hydrogen at a pressure from 1 bar to 4 bar.

Alternatively, in Scheme 2, Step (iii), the nitro intermediate may be reduced to the aniline, for example, by treatment with a tin salt (such as tin chloride) or a metal (such as iron or zinc) in the presence of an acid (such as acetic acid or hydrochloric acid) at a temperature between room temperature and 100° C. A wide range of conditions are known to one skilled in the art for the conversion of a nitro compound to an aniline.

In Scheme 2, Step (iv), an aniline 2D may be converted to a sulfonamide 2E by treatment with an appropriate sulfonyl chloride in the presence of a base (such as pyridine, triethylamine, or di-isopropylethylamine) optionally in a solvent (such as dichloromethane, dimethylformamide, or N-methylpyrrolidinone) at a temperature between room temperature and the reflux temperature of the solvent.

In Scheme 2, Step (v), the benzyl group may be removed from 2D to give a compound of General Formula I. This may be achieved by treating a solution of the benzyl tetrazole in a solvent (such as methanol, ethanol, or ethyl acetate) with a hydrogenation catalyst (such as palladium on carbon, palladium hydroxide on carbon, or platinum on carbon) under an atmosphere of hydrogen at a pressure from 1 bar to 4 bar.

It will be recognized by one skilled in the art that compounds of Formula I, General Formula I, or intermediates towards these compounds may be derivatised further or converted into other compounds by modifications to the substituents by using known standard methods such as substitution, oxidation, or reduction including those interconversions described above for the preparation of compounds of General Formula I.

For example, a carbon-carbon bond may be made by the reaction of a compound in which one of the substituents is an appropriate group (such as a bromine or a trifluoromethanesulfonate) with an organometallic reagent such as a boronic acid, or boronate ester in the presence of a palladium catalyst (such as palladium chloride dppf, tetrakis-triphenylphosphine palladium(0), or bis-palladium tris(dibenzylideneacetone)), in the presence of a base (such as potassium carbonate or cesium carbonate) in an appropriate solvent (such as aqueous dioxane or aqueous tetrahydrofuran) at a temperature between room temperature and the reflux temperature of the solvent or by irradiation in a microwave at a temperature between 100° C. and 160° C.

Alternatively, a carbon-carbon bond may be formed by the reaction of a compound in which one of the substituents is an appropriate group (such as a bromine or a trifluoromethanesulfonate) with a stannane in the presence of a palladium catalyst (such as palladium chloride dppf) in an appropriate solvent (such as dioxane, dimethoxyethane, or tetrahydrofuran) at a temperature between room temperature and the reflux temperature of the solvent or alternatively by irradiation in a microwave at a temperature between 100° C. and 160° C.

Alternatively, a carbon-carbon bond may be formed by the reaction of a compound in which one of the substituents is a leaving group (such as a bromine or a trifluoromethanesulfonate) with an alkene (such as an acrylate) in the presence of a catalyst (such as a palladium catalyst, for example tetrakis-triphenylphosphine palladium(0)) and a base or salt (such as tributylamine or potassium acetate) at a temperature between 80° C. and 120° C. or by irradiation in a microwave at a temperature between 100° C. and 160° C.

Alternatively, a carbon-carbon bond may be formed by the reaction of a compound in which one of the substituents is an appropriate group (such as a bromine or a trifluoromethanesulfonate) with an organozinc reagent in the presence of a catalyst (such as a palladium catalyst, for example tetrakis-triphenylphosphine palladium(0)) and a base or salt (such as tributylamine or potassium acetate) in an appropriate solvent (such as dioxane or tetrahydrofuran) at a temperature between room temperature and the reflux temperature of the solvent or by irradiation in a microwave at a temperature between 100° C. and 160° C.

A carbon-carbon bond may, alternatively, be prepared by the reaction of a compound in which one of the substituents is an appropriate group (such as a bromine or a trifluoromethanesulfonate) with a terminal alkyne in the presence of a palladium catalyst (such as tetrakis(triphenylphosphine) palladium(0)) optionally in the presence of an additional copper catalyst (such as copper(I) iodide) in the presence of a base or salt (such as triethylamine or potassium acetate), in a solvent (such as tetrahydrofuran or N,N-dimethylformamide) at a temperature between room temperature and the reflux temperature of the solvent or by irradiation in a microwave at a temperature between 100° C. and 160° C.

Examples of the formation of carbon-oxygen bonds are known to one skilled in the art, to prepare ethers. Examples of the formation of carbon-oxygen bonds may involve the reaction of an intermediate in which one of the substituents is an aryl halide or aryl sulfonate (such as an aryl fluoride, bromide, or tosylate) with an alcohol or phenol. An alcohol or phenol may be deprotonated, for example by treatment with a base (such as sodium hydride) in a solvent (such as tetrahydrofuran) and then treated with the aryl halide or sulfonate, then stirred at a temperature between room temperature and the reflux temperature of the solvent.

Alternatively an ether may be prepared by the coupling of a phenol with an alcohol in the presence of a phosphine (such as triphenylphosphine) and also in the presence of a dehydrating agent (such as an ester of an azodicarboxylate, for example, the dimethyl, diethyl, or di-isopropyl azodicarboxylate) in a solvent (such as tetrahydrofuran) at a temperature between 0° C. and room temperature.

Further methods of forming a carbon-oxygen bond involve the deprotonation of a phenol by treatment with a base (such as sodium hydride or potassium carbonate) in a solvent (such as tetrahydrofuran or dimethyl formamide) followed by the reaction with an alkylating agent (such as an alkyl halide or alkyl sulfate) and stirring at a temperature between room temperature and the reflux temperature of the solvent.

Examples of the formation of carbon-nitrogen bonds are known to one skilled in the art. For example, a carbon-nitrogen bond may be formed by the alkylation of a primary or secondary amine using a reductive alkylation process. For example, the amine can be treated with an aldehyde and a borohydride (such as sodium triacetoxyborohydride, or sodium cyanoborohydride) in a solvent (such as a halogentaed hydrocarbon, for example dichloromethane), or an alcohol, (for example ethanol) and, where necessary, in the presence of an acid (such as acetic acid).

Another example of the formation of carbon-nitrogen bonds involves the treatment of a compound in which one of the substituents is a leaving group (such as a bromine or a trifluoromethanesulfonate) with an amine in the presence of a palladium catalyst (such as tetrakis-triphenylphosphine palladium(0)) in the presence of a ligand (such as Xantphos) in a solvent (such as toluene) at a temperature between room temperature and the reflux temperature of the solvent or alternatively by irradiation in a microwave at a temperature between 100° C. and 150° C.

Alternatively a carbon-nitrogen bond may be formed by the reaction of an aryl halide (such as an aryl fluoride or aryl bromide) or an aryl sulfonate (such as an aryl tosylate) with an amine in a solvent (such as butanol) at a temperature between room temperature and the reflux temperature of the solvent or by irradiation in a microwave at a temperature between 120° C. and 220° C.

A further example of the conversion of one functional group into another involves the reaction in which an aryl halide may be subjected to halogen-metal exchange by treatment with a base (such as a lithium base, for example n-butyl or t-butyl lithium) optionally at a low temperature (such as −78° C.) in a solvent (such as tetrahydrofuran) and then quenched with an electrophile to introduce a desired substituent. Thus, for example, a formyl group can be introduced by using dimethylformamide as the electrophile.

Particular oxidation approaches include dehydrogenations and aromatisation, decarboxylation and the addition of oxygen to certain functional groups. For example, aldehyde groups can be prepared by oxidation of the corresponding alcohol using conditions well known to those skilled in the art. For example, an alcohol can be treated with an oxidising agent (such as the Dess-Martin reagent) in a solvent (such as a halogenated hydrocarbon, for example dichloromethane).

Alternative oxidising conditions can be used, such as treatment with oxalyl chloride and an activating amount of dimethylsulfoxide and subsequent quenching by the addition of an amine (such as triethylamine). Such a reaction can be carried out in an appropriate solvent (such as a halogentaed hydrocarbon, for example dichloromethane) and under appropriate conditions (such as cooling below room temperature, for example to −78° C. followed by warming to room temperature).

In another example, sulfur atoms can be oxidised to the corresponding sulfoxide or sulfone using an oxidising agent (such as a peroxy acid, for example 3-chloroperoxybenzoic acid) in an inert solvent (such as a halogenated hydrocarbon, for example dichloromethane) at a temperature between room temperature and the reflux temperature of the solvent.

Particular reduction approaches include the removal of oxygen atoms from particular functional groups, saturation (or partial saturation) of unsaturated compounds including aromatic rings. For example, primary alcohols can be generated from the corresponding ester or aldehyde by reduction, using a metal hydride (such as lithium aluminium hydride or sodium borohydride in a solvent such as tetrahydrofuran or methanol).

Alternatively, an alcohol can be generated from the corresponding carboxylic acid by reduction, using a metal hydride (such as lithium aluminium hydride in a solvent such as tetrahydrofuran).

Salts of compounds of Formula I may be prepared by the reaction of a compound of Formula I with an appropriate acid or base in a suitable solvent, or mixture of solvents (such as an ether, for example, diethyl ether, or an alcohol, for example ethanol, or an aqueous solvent) using conventional procedures. Salts of compound of Formula I can be exchanged for other salts by treatment using conventional ion-exchange chromatography procedures.

Where it is desired to obtain a particular enantiomer of a compound of Formula I, this may be produced from a corresponding mixture of enantiomers by employing any suitable conventional procedure for resolving enantiomers. For example, diasteromeric derivatives (such as salts) can be produced by reaction of a mixture of enantiomers of a compound of Formula I (such a racemate) or intermediates towards compounds of Formula I and an appropriate chiral compound (such as a chiral base). The diasteromers can then be separated by any conventional means (such as crystallisation or chromatography) and the desired enantiomer recovered (such as by treatment with an acid in the instance where the diastereomer is a salt). Alternatively, a racemic mixture of esters can be resolved by kinetic hydrolysis using a variety of biocatalysts (for example, see Patel *Steroselective Biocatalysts,* Marcel Decker; New York 2000).

In another resolution process a racemate of compounds of Formula I or intermediates towards compounds of Formula I can be separated using chiral High Performance Liquid Chromatography. Alternatively, a particular enantiomer can be obtained by using an appropriate chiral intermediate in one of the processes described above. Chromatography, recrystallisation, and other conventional separation procedures may also be used with intermediates or final products where it is desired to obtain a particular geometric isomer.

II. Methods

In another aspect, methods of modulating the activity of MetAP2 are provided. Such methods comprise exposing said receptor to a compound described herein. In some embodiments, the compound utilized by one or more of the foregoing methods is one of the generic, subgeneric, or specific compounds described herein, such as a compound of formula I. The ability of compounds described herein to modulate or inhibit MetAP2 can be evaluated by procedures known in the art and/or described herein. In another aspect, methods of treating a disease associated with expression or activity of MetAP2 in a patient are provided. For example, a contemplated method includes administering a disclosed compound in an amount sufficient to establish inhibition of intracellular MetAP2 effective to increase thioredoxin production in the patient and to induce multi organ stimulation of anti-obesity processes in the subject, for example, by administering a disclosed compound in an amount insufficient to reduce angiogenesis in the patient.

In certain embodiments, a method of treating and or ameliorating obesity in a patient by administering an effective amount of a disclosed compound is provided. Also provided herein are methods for inducing weight loss in a patient in need thereof.

Other contemplated methods of treatment include methods of treating or amelioriating an obesity-related condition or co-morbidity, by administering a compound disclosed herein to a subject. For example, contemplated herein are methods for treating type 2 diabetes in a patient in need thereof.

Exemplary co-morbidities include cardiac disorders, endocrine disorders, respiratory disorders, hepatic disorders, skeletal disorders, psychiatric disorders, metabolic disorders, and reproductive disorders.

Exemplary cardiac disorders include hypertension, dyslipidemia, ischemic heart disease, cardiomyopathy, cardiac infarction, stroke, venous thromboembolic disease, and pulmonary hypertension. Exemplary endocrine disorders include type 2 diabetes and latent autoimmune diabetes in adults. Exemplary respiratory disorders include obesity-hypoventilation syndrome, asthma, and obstructive sleep apnea. An exemplary hepatic disorder is nonalcoholic fatty liver disease. Exemplary skeletal disorders include back pain and osteoarthritis of weight-bearing joints. Exemplary metabolic disorders include Prader-Willi Syndrome and polycystic ovary syndrome. Exemplary reproductive disorders include sexual dysfunction, erectile dysfunction, infertility, obstetric complications, and fetal abnormalities. Exemplary psychiatric disorders include weight-associated depression and anxiety.

In particular, in certain embodiments, a method of treating the above medical indications comprising administering to a subject in need thereof a therapeutically effective amount of a compound described herein, such as a compound of formula I, is provided.

Obesity or reference to "overweight" refer to an excess of fat in proportion to lean body mass. Excess fat accumulation is associated with increase in size (hypertrophy) as well as number (hyperplasia) of adipose tissue cells. Obesity is variously measured in terms of absolute weight, weight:height ratio, distribution of subcutaneous fat, and societal and esthetic norms. A common measure of body fat is Body Mass Index (BMI). The BMI refers to the ratio of body weight (expressed in kilograms) to the square of height (expressed in meters). Body mass index may be accurately calculated using either of the formulas: weight(kg)/height$^2$(m$^2$) (SI) or 703× weight(lb)/height$^2$(in$^2$) (US).

In accordance with the U.S. Centers for Disease Control and Prevention (CDC), an overweight adult has a BMI of 25 kg/m$^2$ to 29.9 kg/m$^2$, and an obese adult has a BMI of 30 kg/m$^2$ or greater. A BMI of 40 kg/m$^2$ or greater is indicative of morbid obesity or extreme obesity. Obesity can also refer to patients with a waist circumference of about 102 cm for males and about 88 cm for females. For children, the definitions of overweight and obese take into account age and gender effects on body fat. Patients with differing genetic background may be considered "obese" at a level differing from the general guidelines, above.

The compounds also are useful for reducing the risk of secondary outcomes of obesity, such as reducing the risk of left ventricular hypertrophy. Methods for treating patients at risk of obesity, such as those patients who are overweight, but not obese, e.g. with a BMI of between about 25 and 30 kg/m$^2$, are also contemplated. In certain embodiments, a patient is a human.

BMI does not account for the fact that excess adipose can occur selectively in different parts of the body, and development of adipose tissue can be more dangerous to health in some parts of the body rather than in other parts of the body. For example, "central obesity", typically associated with an "apple-shaped" body, results from excess adiposity especially in the abdominal region, including belly fat and visceral fat, and carries higher risk of co-morbidity than "peripheral obesity", which is typically associated with a "pear-shaped" body resulting from excess adiposity especially on the hips. Measurement of waist/hip circumference ratio (WHR) can be used as an indicator of central obesity. A minimum WHR indicative of central obesity has been variously set, and a centrally obese adult typically has a WHR of about 0.85 or greater if female and about 0.9 or greater if male.

Methods of determining whether a subject is overweight or obese that account for the ratio of excess adipose tissue to lean body mass involve obtaining a body composition of the subject. Body composition can be obtained by measuring the thickness of subcutaneous fat in multiple places on the body, such as the abdominal area, the subscapular region, arms, buttocks and thighs. These measurements are then used to estimate total body fat with a margin of error of approximately four percentage points. Another method is bioelectrical impedance analysis (BIA), which uses the resistance of electrical flow through the body to estimate body fat. Another method is using a large tank of water to measure body buoyancy. Increased body fat will result in greater buoyancy, while greater muscle mass will result in a tendency to sink.

In another aspect, methods for treating an overweight or obese subject involving determining a level of at least one biomarker related to being overweight or obese in the subject, and administering an effective amount of a disclosed compound to achieve a target level in the subject are provided. Exemplary biomarkers include body weight, Body Mass Index (BMI), Waist/Hip ratio WHR, plasma adipokines, and a combination of two or more thereof.

In certain embodiments, the compound utilized by one or more of the foregoing methods is one of the generic, subgeneric, or specific compounds described herein, such as a compound of formula I.

The compounds may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, a compound may be administered orally, subcutaneously, topically, parenterally, by inhalation spray or rectally in dosage unit formulations containing conventional non-toxic pharmaceutically acceptable carriers, adjuvants, and vehicles. Parenteral administration may include subcutaneous injections, intravenous or intramuscular injections, or infusion techniques.

Treatment can be continued for as long or as short a period as desired. The compositions may be administered on a regimen of, for example, one to four or more times per day. A suitable treatment period can be, for example, at least about one week, at least about two weeks, at least about one month, at least about six months, at least about 1 year, or indefinitely. A treatment period can terminate when a desired result, for example a weight loss target, is achieved. A treatment regimen can include a corrective phase, during which dose sufficient to provide reduction of weight is administered, and can be followed by a maintenance phase, during which a e.g. lower dose sufficient to prevent weight gain is administered. A suitable maintenance dose is likely to be found in the lower parts of the dose ranges provided herein, but corrective and maintenance doses can readily be established for individual subjects by those of skill in the art without undue experimentation, based on the disclosure herein. Maintenance doses can be employed to maintain body weight in subjects whose body weight has been previously controlled by other means, including diet and exercise, bariatric procedures such as bypass or banding surgeries, or treatments employing other pharmacological agents.

III. Pharmaceutical Compositions and Kits

In another aspect, pharmaceutical compositions comprising compounds as disclosed herein formulated together with a pharmaceutically acceptable carrier provided. In particular, the present disclosure provides pharmaceutical compositions comprising compounds as disclosed herein formulated together with one or more pharmaceutically acceptable carriers. These formulations include those suitable for oral, rectal, topical, buccal, parenteral (e.g., subcutaneous, intramuscular, intradermal, or intravenous) rectal, vaginal, or aerosol administration, although the most suitable form of administration in any given case will depend on the degree and severity of the condition being treated and on the nature of the particular compound being used. For example, disclosed compositions may be formulated as a unit dose, and/or may be formulated for oral or subcutaneous administration.

Exemplary pharmaceutical compositions may be used in the form of a pharmaceutical preparation, for example, in solid, semisolid, or liquid form, which contains one or more of the compounds, as an active ingredient, in admixture with an organic or inorganic carrier or excipient suitable for external, enteral, or parenteral applications. The active ingredient may be compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets, the principal active ingredient may be mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a compound, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars, or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants In another aspect, enteral pharmaceutical formulations including a disclosed compound, an enteric material; and a pharmaceutically acceptable carrier or excipient thereof are provided. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleat, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure would recognize that it is not comprehensive and that there are other enteric materials that may be used.

Advantageously, kits are provided for use by, for example, a consumer in need of weight loss. Such kits include a suitable dosage form such as those described above and instructions describing the method of using such dosage form to mediate, reduce, or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a first compound can consist of one tablet or capsule while a daily dose of the second compound can consist of several tablets or capsules and vice versa. The memory aid should reflect this.

Also contemplated herein are methods and compositions that include a second active agent, or administering a second active agent. For example, in addition to being overweight or obese, a subject or patient can further have overweight- or obesity-related co-morbidities, i.e., diseases and other adverse health conditions associated with, exacerbated by, or precipitated by being overweight or obese. Contemplated herein are disclosed compounds in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-515). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol).

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497):1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34:1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9): 978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2):104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125:1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6:1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese. van Saase (J Rheumatol (1988) 15(7):1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8:1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), Urofollitropin, Heparin, Follitropin alfa, and Follitropin beta.

Weiss et al. (American Journal of Obstetrics and Gynecology (2004) 190(4):1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7): 824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

In another aspect methods for facilitating and maintaining weight loss in a subject involving administering to the subject an amount of a disclosed compound effective to result in weight loss in the subject and administering a therapeutically effective amount of a different weight loss agent to maintain a reduced weight in the subject are provided. Weight loss agents include serotonin and noradrenergic re-uptake inhibitors; noradrenergic re-uptake inhibitors; selective serotonin re-uptake inhibitors; and intestinal lipase inhibitors. Particular weight loss agents include orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl CoA desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

At least some of the compounds identified as "Intermediates" herein are contemplated as active ingredients. For example, at least some of the compounds identified as "Intermediates" herein may be modulators of MetAP2

$^1$H NMR spectra were recorded at ambient temperature using a Varian Unity Inova (400 MHz) spectrometer with a triple resonance 5 mm probe for Example compounds, and either a Bruker Avance DRX (400 MHz) spectrometer or a Bruker Avance DPX (300 MHz) spectrometer for Intermediate compounds. Chemical shifts have been expressed in ppm relative to tetramethylsilane. The following abbreviations have been used: br=broad signal, s=singlet, d=doublet, dd=double doublet, dt=double triplet, t=triplet, q=quartet, m=multiplet.

Mass Spectrometry (LCMS) experiments to determine retention times and associated mass ions were performed using the following methods:

Method A: Experiments were performed on a Waters Micromass ZQ2000 quadrupole mass spectrometer with an electrospray source operating in positive and negative ion mode linked to a Waters Acquity UPLC system. Detection was achieved using a PDA UV detector. The LC column was an Acquity BEH 1.7 micron C18 100×2.1 mm. The flow rate was 0.4 mL/minute. The initial solvent system was 95% water containing 0.1% formic acid (solvent A) and 5% acetonitrile containing 0.1% formic acid (solvent B) and was held constant for 0.4 minutes followed by a gradient up to 5% solvent A and 95% solvent B over the next 6 minutes. The final solvent system was held constant for a further 0.8 minutes.

Method B: Experiments were performed on a Waters Micromass ZQ2000 quadrupole mass spectrometer with an electrospray source operating in positive and negative ion mode linked to a Hewlett Packard HP1100 LC system. Detection was achieved using a DAD UV detector and a Sedex 85 evaporative light scattering detector The LC column was a Higgins Clipeus 5 micron C18 100×3.0 mm The flow rate was 1 mL/minute. The initial solvent system was 95% water containing 0.1% formic acid (solvent A) and 5% acetonitrile containing 0.1% formic acid (solvent B) and was held constant for 1 minute followed by a gradient up to 5% solvent A and 95% solvent B over the next 12 minutes. The final solvent system was held constant for a further 7 minutes.

Method C: Experiments were performed on a Waters ZMD quadrupole mass spectrometer with an electrospray source operating in positive and negative ion mode linked to a Waters 1525 LC system. Detection was achieved using a Waters 996 diode array detector and a Sedex 85 evaporative light scattering detector. The LC column was a Luna 3 micron C18(2) 30×4.6 mm. The flow rate was 2 mL/minute. The initial solvent system was 95% water containing 0.1% formic acid (solvent A) and 5% acetonitrile containing 0.1% formic acid (solvent B) and was held constant for 0.5 minute followed by a gradient up to 5% solvent A and 95% solvent B over the next 4 minutes. The final solvent system was held constant for a further 1 minute.

Method D: Experiments were performed on a Finnigan AQA single quadrupole mass spectrometer with an electrospray source operating in positive ion mode linked to a Hewlett Packard 1050 LC system. Detection was achieved using a UV diode array detector and a Sedex 65 evaporative light scattering detector. The LC column was a Luna 3 micron C18(2) 30×4.6 mm. The flow rate was 2 mL/minute. The initial solvent system was 95% water containing 0.1% formic acid (solvent A) and 5% acetonitrile containing 0.1% formic acid (solvent B) and was held constant for 0.5 minutes followed by a gradient up to 5% solvent A and 95% solvent B over the next 4 minutes. The final solvent system was held constant for a further 1 minute.

Method E: Experiments were performed on a Waters Platform LC quadrupole mass spectrometer with an electrospray source operating in positive and negative ion mode linked to a Hewlett Packard HP1100 LC system. Detection was achieved using both a diode array detector and a Sedex 85 evaporative light scattering detector. The LC column was a Phenomenex Luna 3 micron C18(2) 30×4.6 mm. The flow rate was 2 mL/minute. The initial solvent system was 95% water containing 0.1% formic acid (solvent A) and 5% acetonitrile containing 0.1% formic acid (solvent B) and was held constant for 0.5 minutes followed by a gradient up to 5% solvent A and 95% solvent B over the next 4 minutes. The final solvent system was held constant for a further 1 minute. Microwave experiments were carried out using a Biotage Initiator™, which uses a single-mode resonator and dynamic field tuning, both of which give reproducibility and control. Temperatures from 40-250° C. can be achieved, and pressures of up to 20 bars can be reached. Three types of vial are available for this processor, 0.5-2.0 ml, 2.0-5.0 ml and 5.0-20 ml.

Preparative HPLC purification was carried out using either a C18-reverse-phase column from Genesis (C18) (100×22.5 mm with 7 micron particle size, UV detection at 230 or 254 nm, flow 5-15 mL/min), eluting with gradients from 100-0 to 0-100% water/acetonitrile containing 0.1% formic acid. Fractions containing the required product (identified by LCMS analysis) were pooled, the organic fraction removed by evaporation, and the remaining aqueous fraction lyophilised, to give the final product.

Compounds which required column chromatography were purified using either a Biotage SP1™ Flash Purification system with Touch Logic Control or a Combiflash Companion® with pre-packed silica gel Isolute® SPE cartridge, Biotage SNAP cartridge or Redisep® Rf cartridge respectively.

Abbreviations: AIBN: Azo-bis-(isobutyronitrile); DCM: Dichloromethane; DIPEA: Diisopropylethylamine; DMF: N,N-Dimethylformamide; HATU: 2-(7-Aza-1H-benzotriazol-1-yl)-1,1,3,3-tetramethyluronium hexafluorophosphate; NMP: 1-Methyl-2-pyrrolidone; THF: Tetrahydrofuran; Xantphos: 4,5-Bis(diphenylphosphino)-9,9-dimethylxanthene.

Example 1

N-[1-(1H-Tetrazol-5-yl)-5,6,7,8-tetrahydronaphthalen-2-yl]-benzenesulfonamide

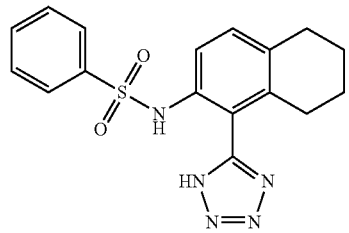 [SMILES: O=S(=O)(Nc1ccc2c(c1-c1nnn[nH]1)CCCC2)c1ccccc1]

Tri-n-butyl tin chloride (0.16 mL) was added to a solution of sodium azide (0.039 g) in DMF (0.6 mL) and the mixture was stirred for 5 minutes. Tetra-butyl ammonium bromide (0.0065 g) was then added, followed by N-(1-cyano-5,6,7,8-tetrahydronaphthalen-2-yl)benzenesulfonamide (Intermediate 1, 0.177 g). The mixture was heated by microwave irradiation at 220° C. for 1 hour. The solution was then acidified with 1N hydrochloric acid and the products were extracted into DCM, dried with magnesium sulfate and filtered. The filtrate was evaporated to dryness and the residue was purified by preparative HPLC (C18). The fractions containing the desired product were combined, and the solvent was removed by evaporation to give the title compound as a beige solid (0.01 g).

LCMS (Method B) r/t 9.46 min (M+H) 356
NMR (CD$_3$OD) δ 7.04 (t, 1H), 6.99-6.85 (m, 4H), 6.76-6.68 (m, 2H), 2.32 (m, 2H), 1.97 (m, 2H), 1.34-1.15 (m, 4H)

Example 2

N-[3-Cyclopropyl-2-(1H-tetrazol-5-yl)-phenyl]-benzenesulfonamide

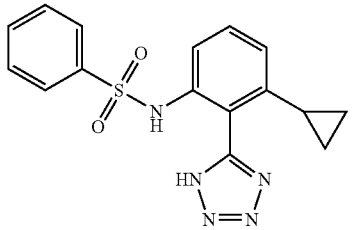 [SMILES: O=S(=O)(Nc1cccc(C2CC2)c1-c1nnn[nH]1)c1ccccc1]

N-(2-Cyano-3-cyclopropylphenyl)-benzenesulfonamide (Intermediate 9, 0.052 g), azidotrimethyl-silane (0.087 g) and dibutyltin oxide (0.038 g) were suspended in 1,2-dichloroethane (3 mL). The mixture was heated by microwave irradiation at 140° C. for 45 minutes. Six further aliquots of azidotrimethylsilane (0.174 g) were added and after each addition the mixture was heated by microwave irradiation at 140° C. for 60 minutes. The reaction mixture was acidified to pH 1 using 1N hydrochloric acid, and then extracted with ethyl acetate. The combined organic extracts were dried with magnesium sulfate, filtered and the filtrate was evaporated under vacuum. The residue was triturated with a mixture of pentane and cyclohexane and the solid was collected by filtration, to give the title compound as a white solid (0.039 g).

LCMS (Method A) r/t 3.97 min (M+H) 342

NMR (DMSO-$d_6$) δ 9.79 (br s, 1H), 7.65-7.61 (m, 2H), 7.59 (t, 1H), 7.53-7.47 (m, 2H), 7.26 (t, 1H), 6.86 (d, 1H), 6.82 (d, 1H), 1.49-1.39 (br m, 1H), 0.69-0.63 (m, 2H), 0.51-0.46 (m, 2H)

Example 3

N-[3-Methoxy-2-(1H-tetrazol-5-yl)-phenyl]-benzenesulfonamide

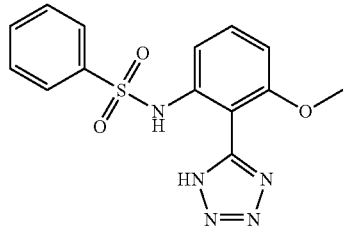 [SMILES: COc1cccc(NS(=O)(=O)c2ccccc2)c1-c1nnn[nH]1]

A mixture of N-[2-(1-benzyl-1H-tetrazol-5-yl)-3-methoxyphenyl]-benzenesulfonamide (Intermediate 12, 0.104 g), ammonium formate (0.45 g) and palladium hydroxide (0.01 g) in ethanol (10 mL) was heated at reflux for 72 hours. The reaction mixture was filtered through celite and the filtrate was evaporated under vacuum. The residue was purified by flash chromatography on silica, eluting with a mixture of DCM and methanol. The fractions containing the desired product were combined and evaporated to give the title compound as a colorless solid (0.05 g).

LCMS (Method A) r/t 4.18 min (M+H) 332

NMR (DMSO-$d_6$) δ 10.99 (s, 1H), 7.68-7.63 (m, 2H), 7.55 (t, 1H), 7.48-7.40 (m, 3H), 7.07 (d, 1H), 6.93 (d, 1H), 3.82 (s, 3H)

Example 4

N-[3-Methyl-2-(1H-tetrazol-5-yl)-phenyl]-benzenesulfonamide

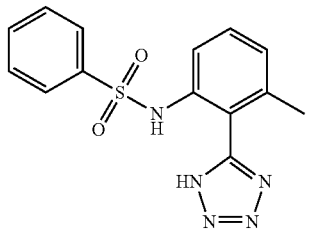 [SMILES: Cc1cccc(NS(=O)(=O)c2ccccc2)c1-c1nnn[nH]1]

N-[2-(1-Benzyl-1H-tetrazol-5-yl)-3-methylphenyl]-benzenesulfonamide (Intermediate 15, 0.05 g) was dissolved in ethyl acetate (10 mL) under a nitrogen atmosphere. Palladium on carbon (10%, 0.02 g) was added and the nitrogen atmosphere was replaced by hydrogen. The mixture was stirred for 7 days and then filtered through celite and the solvent was removed by evaporation under vacuum. The residue was purified by preparative HPLC (C18). The fractions containing the desired product were combined, and the solvent was removed by evaporation to give the title compound as a white solid (0.08 g).

LCMS (Method A) r/t 3.66 min (M+H) 316

NMR (DMSO-$d_6$) δ 9.91 (s, 1H), 7.63-7.55 (m, 3H), 7.51-7.46 (m, 2H), 7.25 (t, 1H), 7.13 (d, 1H), 6.88 (d, 1H), 2.02 (s, 3H)

Example 5

N-[3-Bromo-2-(1H-tetrazol-5-yl)-phenyl]-benzenesulfonamide

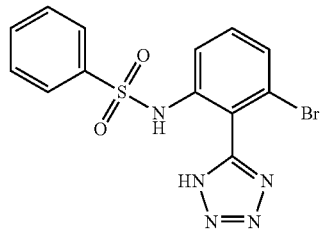 [SMILES: O=S(=O)(Nc1cccc(Br)c1-c1nnn[nH]1)c1ccccc1]

A solution of N-(3-Bromo-2-cyanophenyl)-benzenesulfonamide (Intermediate 21, 0.22 g) and tributyltin azide (0.43 g) in 1,2-dichlorobenzene (1.5 mL) was heated by microwave irradiation at 130° C. for 2 hours. The mixture was diluted with ether and extracted with aqueous 1M sodium hydroxide. The aqueous solution was acidified with 1N hydrochloric acid to pH 1 and then extracted with ethyl acetate. The organic solution was washed with brine and then dried with sodium sulfate, filtered and the filtrate was evaporated. The residue was triturated with ether and the solid was collected by filtration to give the title compound as a colorless solid (0.19 g).

LCMS (Method A) r/t 3.76 min (M+H) 381

NMR (DMSO-$d_6$) δ 10.03 (br s, 1H), 7.69-7.65 (m, 2H), 7.64-7.59 (m, 1H), 7.58-7.50 (m, 3H), 7.35 (t, 1H), 7.11 (d, 1H)

Intermediate 1

N-(1-Cyano-5,6,7,8-tetrahydronaphthalen-2-yl)benzenesulfonamide

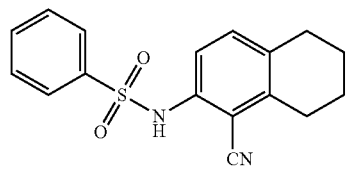 [SMILES: N#Cc1c(NS(=O)(=O)c2ccccc2)ccc2c1CCCC2]

2-Benzenesulfonylamino-5,6,7,8-tetrahydronaphthalene-1-carboxylic acid amide (Intermediate 2, 1.2 g) was dissolved in dry DCM (20 mL) and phosphorous pentachloride (0.9 g) was added. The mixture was stirred for 3 hours then saturated aqueous sodium hydrogencarbonate was added carefully and the products were extracted into ethyl acetate. The organic solution was dried with magnesium sulfate, filtered and the solvent was removed by evaporation. The residue was purified by chromatography on silica, eluting with a mixture of ethyl acetate and cyclohexane. The fractions containing the desired product were combined and the solvent was evaporated to give the title compound as an off-white solid.

LCMS (Method B) r/t 10.35 min (M+H) 313

NMR (DMSO-d$_6$) δ 10.33 (br s 1H), 7.80-7.39 (br m, 5H), 7.28-7.12 (br m, 1H), 6.75-6.55 (br m, 1H), 2.80-2.50 (br m, 4H), 1.83-1.50 (br m, 4H)

Intermediate 2

2-Benzenesulfonylamino-5,6,7,8-tetrahydronaphthalene-1-carboxylic acid amide

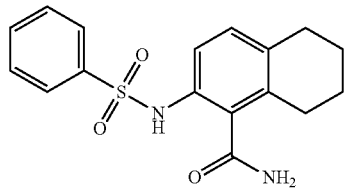 [SMILES: NC(=O)c1c(NS(=O)(=O)c2ccccc2)ccc2c1CCCC2]

2-Benzenesulfonylamino-5,6,7,8-tetrahydronaphthalene-1-carboxylic acid (Intermediate 3, 0.5 g) was suspended in DCM (10 mL) and oxalyl chloride (0.15 mL) was added along with DMF (one drop). The mixture was stirred for 30 minutes, then concentrated under vacuum. The residue was dissolved in dry THF (20 mL) and added slowly to a solution of ammonia in THF. After stirring for 1 hour, the solution was concentrated under vacuum and the residue was triturated with diethyl ether and the solid collected by filtration to give the title compound as a white powder (0.48 g).

NMR (CDCl$_3$) δ 7.84-7.80 (m, 3H), 7.56 (t, 1H), 7.50-7.44 (m, 2H), 7.04-6.98 (m, 2H), 5.78 (br m, 2H), 2.75-2.67 (m, 4H), 1.78-1.68 (m, 4H)

Intermediate 3

2-Benzenesulfonylamino-5,6,7,8-tetrahydronaphthalene-1-carboxylic acid

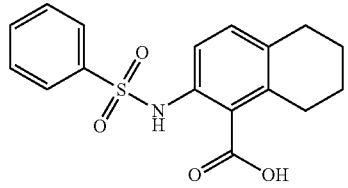 [SMILES: O=C(O)c1c(NS(=O)(=O)c2ccccc2)ccc2c1CCCC2]

2-Benzenesulfonylamino-5,6,7,8-tetrahydronaphthalene-1-carboxylic acid methyl ester (Intermediate 4, 0.68 g) was dissolved in dioxane (12 mL) and a solution of lithium hydroxide monohydrate (0.6 g) in water (6 mL) was added. The mixture was heated by microwave irradiation at 160° C. for 15 minutes then diluted with 1N hydrochloric acid. The product was extracted into DCM and the organic solution was separated, dried with magnesium sulfate, filtered and the filtrate was concentrated under vacuum to give the title compound as a white powder.

NMR (CDCl$_3$) δ 8.64 (br s, 1H), 7.78-7.72 (m, 2H), 7.55 (t, 1H), 7.47-7.36 (m, 3H), 7.16 (d, 1H), 2.84 (t, 2H), 2.75 (t, 2H), 1.79-1.69 (m, 4H)

Intermediate 4

2-Benzenesulfonylamino-5,6,7,8-tetrahydronaphthalene-1-carboxylic acid methyl ester

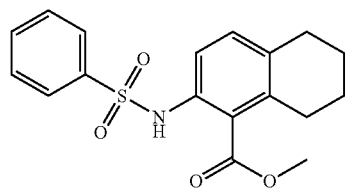 [SMILES: COC(=O)c1c(NS(=O)(=O)c2ccccc2)ccc2c1CCCC2]

To a solution of 2-amino-5,6,7,8-tetrahydronaphthalene-1-carboxylic acid methyl ester (Intermediate 5, 1.5 g) in pyridine (20 mL) was added benzenesulfonyl chloride (0.95 mL). The mixture was stirred for 1 hour then concentrated under vacuum. The residue was dissolved in ethyl acetate and washed with 1N hydrochloric acid, dried with magnesium sulfate and filtered. The filtrate was evaporated under vacuum to give the title compound as an off-white crystalline solid (2.4 g).

NMR (CDCl$_3$) δ 8.17 (br s, 1H), 7.69-7.65 (m, 2H), 7.52 (t, 1H), 7.44-7.37 (m, 3H), 7.13 (d, 1H), 3.63 (s, 3H), 2.73 (t, 2H), 2.65 (t, 2H), 1.76-1.63 (m, 4H)

Intermediate 5

2-amino-5,6,7,8-tetrahydronaphthalene-1-carboxylic acid methyl ester

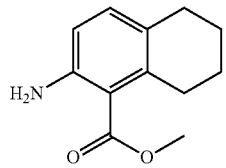

2-(Benzhydrylideneamino)-5,6,7,8-tetrahydronaphthalene-1-carboxylic acid methyl ester (Intermediate 6, 8.2 g) was dissolved in THF (100 mL) and 1N hydrochloric acid was added (100 mL). The mixture was stirred for 1 hour and then passed through an SCX-2 SPE column. The column was washed with acetonitrile and then the desired product was eluted with a solution of 2M ammonia in methanol. Evaporation of the solvent gave the title compound as a clear oil (2.8 g) which was used without further purification or analysis.

Intermediate 6

2-(Benzhydrylideneamino)-5,6,7,8-tetrahydronaphthalene-1-carboxylic acid methyl ester

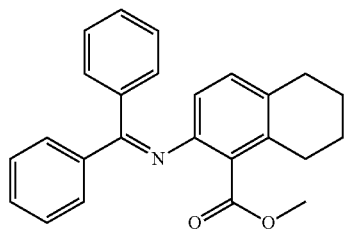 [SMILES: COC(=O)c1c(N=C(c2ccccc2)c2ccccc2)ccc2c1CCCC2]

Cesium carbonate (12.4 g), palladium (II) acetate (0.12 g), triethylamine (0.12 mL) and Xantphos (0.474 g) were suspended in dioxane (50 mL) under nitrogen. 2-Trifluoromethanesulfonyloxy-5,6,7,8-tetrahydronaphthalene-1-carboxylic acid methyl ester (Intermediate 7, 4.2 g) and benzhydrylidenamine (5.5 mL) in dioxane (35 mL) were added and the mixture was heated at 100° C. for 3.5 hours. The resulting mixture was partitioned between ethyl acetate and water. The organic solution was washed with water and concentrated under vacuum. The residue was recrystallised from methanol to give the title compound as an off-white solid (8.2 g).

LCMS (Method C) r/t 5.00 min (M+H) 370

Intermediate 7

2-Trifluoromethanesulfonyloxy-5,6,7,8-tetrahydronaphthalene-1-carboxylic acid methyl ester

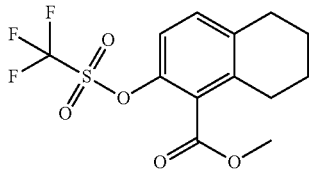 [SMILES: COC(=O)c1c(OS(=O)(=O)C(F)(F)F)ccc2c1CCCC2]

2-Hydroxy-5,6,7,8-tetrahydronaphthalene-1-carboxylic acid methyl ester (Intermediate 8, 6 g) was dissolved in DCM (100 mL) and pyridine (6.5 mL). The solution was cooled to −20° C. and trifluoromethanesulfonic anhydride (6.5 mL) was added dropwise over 15 minutes. The mixture was stirred at −20° C. for a further 20 minutes, then allowed to warm to room temperature and stirred for a further 60 minutes. t-Butyl methyl ether (200 mL) was added and the resulting mixture was filtered. The filtrate was washed with 2N hydrochloric acid, water and then with brine before being dried with magnesium sulfate and filtered. The filtrate was concentrated under vacuum to give the title compound as a yellow oil (9.2 g).

LCMS (Method C) r/t 4.74 min (M+H) 339, (M+Na) 361

Intermediate 8

2-Hydroxy-5,6,7,8-tetrahydro-naphthalene-1-carboxylic acid methyl ester

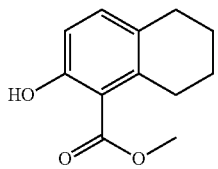

Under an atmosphere of nitrogen, platinum oxide (5 g) was added to a solution of 2-hydroxy-naphthalene-1-carboxylic acid methyl ester (10 g) in acetic acid (200 mL). The nitrogen atmosphere was replaced by hydrogen, the pressure was increased to 4 bar and the mixture was stirred overnight. The resulting suspension was filtered and the filtrate was concentrated under vacuum to give an oil. The residue was purified by chromatography on silica, eluting with DCM. The fractions containing the desired product were combined and evaporated under vacuum to give the title compound as a colorless oil (11.7 g).

LCMS (Method C) r/t 4.31 min (M+H) 207

Intermediate 9

N-(2-Cyano-3-cyclopropylphenyl)-benzenesulfonamide

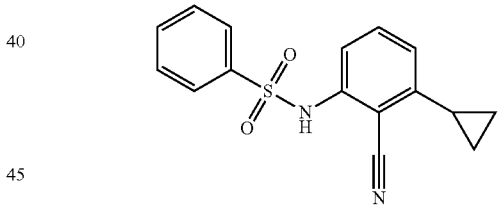

Benzenesulfonyl chloride (0.093 g) was added to a solution of 2-amino-6-cyclopropyl-benzonitrile (Intermediate 10, 0.07 g) in DCM (4 mL) and pyridine (0.1 mL). The mixture was stirred for 5 hours, then a further aliquot of benzenesulfonyl chloride (0.093 g) was added together with triethylamine (0.12 mL) and the mixture was stirred overnight. The reaction mixture was washed with water, and the organic solution was dried with magnesium sulfate, filtered and the filtrate was evaporated under vacuum. The residue was purified by flash chromatography on silica, eluting with a mixture of ethyl acetate and cyclohexane. The fractions containing the desired product were combined and evaporated to give the title compound as a colorless oil (0.052 g).

LCMS (Method D) r/t 4.07 min (M+H) 299

NMR (CDCl$_3$) δ 7.86-7.81 (m, 2H), 7.58 (t, 1H), 7.52-7.45 (m, 3H), 7.38 (t, 1H), 7.04 (br s, 1H), 6.65 (d, 1H), 2.12-2.04 (m, 1H), 1.12-1.05 (m, 2H), 0.75-0.68 (m, 2H)

Intermediate 10

2-Amino-6-cyclopropylbenzonitrile

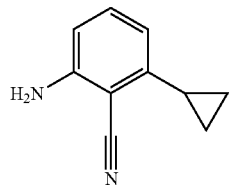

A slurry of palladium on carbon (10%; 0.025 g) in DCM (5 mL) was added to a solution of 2-nitro-6-cyclopropylbenzonitrile (Intermediate 11, 0.25 g) in ethanol (15 mL) under nitrogen. The nitrogen atmosphere was exchanged for hydrogen and the mixture was stirred for 48 hours. The mixture was filtered and the filtrate was concentrated under vacuum. The residue was purified by flash chromatography on silica, eluting with a mixture of ethyl acetate and cyclohexane. The fractions containing the desired product were combined and evaporated to give the title compound as a colorless oil (0.082 g).

NMR (CDCl$_3$) δ 7.18 (t, 1H), 6.53 (d, 1H), 6.26 (d, 1H), 4.8-4.0 (br m, 2H), 2.20-2.10 (m, 1H), 1.10-1.02 (m, 2H), 0.78-0.70 (m, 2H)

Intermediate 11

2-Nitro-6-cyclopropylbenzonitrile

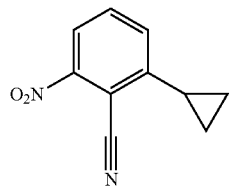 [SMILES: N#Cc1c(C2CC2)cccc1[N+](=O)[O-]]

2-Bromo-6-nitrobenzonitrile (0.56 g), cyclopropyl boronic acid (0.63 g), palladium (II) acetate (0.055 g), tricyclohexylphosphine (0.135 g) and potassium phosphate tribasic (2.36 g) were dissolved in a mixture of toluene (15 mL) and water (3 mL). The mixture was heated at 100° C. under nitrogen for 18 hours. The mixture was cooled and then partitioned between water and DCM. The organic solution was separated, dried with magnesium sulfate, filtered and the solvent was removed under vacuum. The residue was purified by flash chromatography on silica, eluting with a mixture of ethyl acetate and cyclohexane. The fractions containing the desired product were combined and evaporated to give the title compound as a light yellow solid (0.51 g).

NMR (CDCl$_3$) δ 8.05 (d, 1H), 7.64 (t, 1H), 7.27 (d, 1H), 2.52-2.45 (m, 1H), 1.33-1.26 (m, 2H), 0.91-0.85 (m, 2H)

Intermediate 12

N-[2-(1-Benzyl-1H-tetrazol-5-yl)-3-methoxyphenyl]-benzene sulfonamide

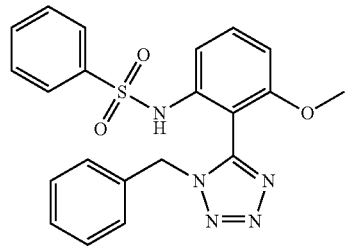 [SMILES: COc1cccc(NS(=O)(=O)c2ccccc2)c1-c1nnnn1Cc1ccccc1]

2-(1-Benzyl-1H-tetrazol-5-yl)-3-methoxyphenylamine (Intermediate 13, 0.115 g) was dissolved in pyridine (0.16 mL) and DCM (2 mL). Benzenesulfonyl chloride (0.08 g) was added and the mixture was stirred overnight. The reaction mixture was diluted with DCM and washed with 1N hydrochloric acid, dried with magnesium sulfate and filtered. The filtrate was evaporated to dryness and the residue was purified by flash chromatography on silica, eluting with a mixture of DCM and methanol. The fractions containing the desired product were combined and evaporated to give the title compound as a colorless solid (0.11 g).

LCMS (Method E) r/t 3.55 min (M+H) 422

Intermediate 13

2-(1-Benzyl-1H-tetrazol-5-yl)-3-methoxyphenylamine

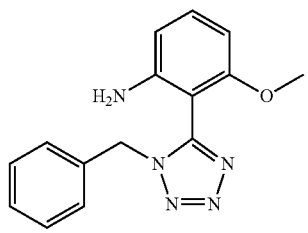

1-Benzyl-5-(2-methoxy-6-nitrophenyl)-1H-tetrazole (Intermediate 14, 0.14 g) was dissolved in ethanol (5 mL) under a nitrogen atmosphere. Platinum on carbon (10%, 0.01 g) was added and the nitrogen atmosphere was replaced by hydrogen. The mixture was stirred for 18 hours and then filtered through celite. The filtrate was evaporated to dryness to give the title compound as a brown gum (0.12 g).

LCMS (Method E) r/t 3.18 min (M+H) 282

Intermediate 14

1-Benzyl-5-(2-methoxy-6-nitrophenyl)-1H-tetrazole

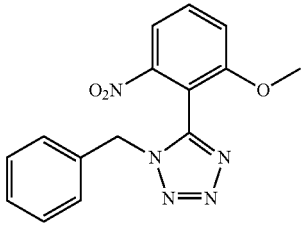 [SMILES: COc1cccc([N+](=O)[O-])c1-c1nnnn1Cc1ccccc1]

1-Benzyl-5-(2-fluoro-6-nitrophenyl)-1H-tetrazole (Intermediate 18, 0.3 g) was dissolved in DCM (4 mL) and a solution of sodium methoxide in methanol (20%; 2 mL) was added. The mixture was stirred for 4 hours and then the solvent was removed by evaporation under vacuum. The residue was dissolved in ethyl acetate and washed with 1N hydrochloric acid and then brine. The organic solution was dried with sodium sulfate, filtered and the solvent was removed by evaporation under vacuum. The residue was purified by flash chromatography on silica, eluting with a mixture of DCM and methanol. The fractions containing the desired product were combined and evaporated to give the title compound as a pale yellow solid (0.14 g).

LCMS (Method E) r/t 3.30 min (M+H) 312

Intermediate 15

N-[2-(1-Benzyl-1H-tetrazol-5-yl)-3-methylphenyl]-benzenesulfonamide

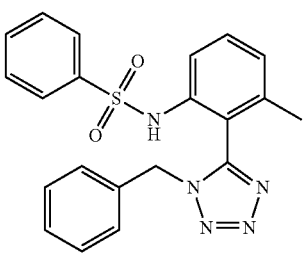 [SMILES: Cc1cccc(NS(=O)(=O)c2ccccc2)c1-c1nnnn1Cc1ccccc1]

2-(1-Benzyl-1H-tetrazol-5-yl)-3-methylphenylamine (Intermediate 16, 0.15 g) was dissolved in pyridine (5 mL) and benzenesulfonyl chloride (0.07 g, 0.4 mmol) was added. The mixture was stirred overnight, then diluted with ethyl acetate and washed with 1N hydrochloric acid, dried with magnesium sulfate and filtered. The filtrate was evaporated to dryness and the residue was purified by flash chromatography on silica, eluting with a mixture of ethyl acetate and cyclohexane. The fractions containing the desired product were combined and evaporated to give the title compound as a white powder (0.16 g).

LCMS (Method A) r/t 4.68 min (M+H) 406

NMR (DMSO-$d_6$) δ 10.03 (s, 1H), 7.75 (m, 1H), 7.73 (m, 1H), 7.66-7.53 (m, 3H), 7.29 (t, 1H), 7.25-7.16 (m, 3H), 7.03 (d, 1H), 6.96-6.92 (m, 2H), 6.83 (d, 1H), 5.36 (dd, 2H), 1.46 (s, 3H)

Intermediate 16

2-(1-Benzyl-1H-tetrazol-5-yl)-3-methylphenylamine

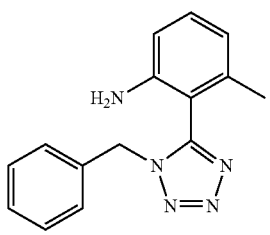

1-Benzyl-5-(2-methyl-6-nitrophenyl)-1H-tetrazole (Intermediate 17, 0.1 g) was dissolved in ethyl acetate (20 mL) under a nitrogen atmosphere. Palladium on carbon (10%, 0.1 g) was added and the nitrogen atmosphere was replaced by hydrogen. The mixture was stirred for 4 hours and then filtered through celite. The solvent was removed by evaporation under vacuum to give the title compound as a white solid (0.09 g).

LCMS (Method E) r/t 3.30 min (M+H) 266

Intermediate 17

1-Benzyl-5-(2-methyl-6-nitrophenyl)-1H-tetrazole

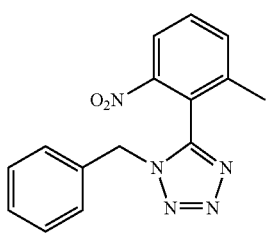 [SMILES: Cc1cccc([N+](=O)[O-])c1-c1nnnn1Cc1ccccc1]

Phosphorous pentachloride (0.42 g, 2 mmol) was added to a solution of N-benzyl-2-methyl-6-nitrobenzamide (Intermediate 19, 0.54 g) in DCM (10 mL). The mixture was stirred under nitrogen for 30 minutes and then azidotrimethylsilane (0.48 g) was added and the mixture was stirred for a further 72 hours. The mixture was diluted with DCM (50 mL) and water (50 mL). Solid sodium bicarbonate was then added to the mixture until there was no further gaseous evolution. The organic solution was washed with saturated aqueous sodium bicarbonate, then with 1N hydrochloric acid, dried with magnesium sulfate and filtered. The solvent was evaporated to give an orange solid which was recrystallised from ethyl acetate to give the title compound as a white solid (0.42 g).

LCMS (Method E) r/t 3.37 min (M+H) 296

NMR (DMSO-$d_6$) δ 8.20 (d, 1H), 7.83-7.73 (m, 2H), 7.27-7.20 (m, 3H), 7.07-7.04 (m, 2H), 5.47 (d, 2H), 1.6 (s, 3H)

By proceeding in a similar manner the following compound was prepared from the appropriate starting materials:

Intermediate 18

1-Benzyl-5-(2-fluoro-6-nitrophenyl)-1H-tetrazole

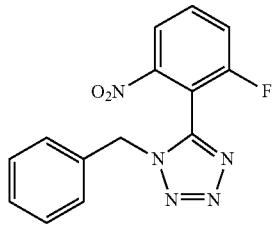 [SMILES: O=[N+]([O-])c1cccc(F)c1-c1nnnn1Cc1ccccc1]

Starting from N-benzyl-2-fluoro-6-nitrobenzamide (Intermediate 20) and used without further characterisation.

Intermediate 19

N-Benzyl-2-methyl-6-nitrobenzamide

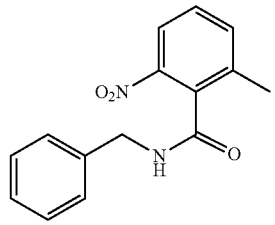 [SMILES: Cc1cccc([N+](=O)[O-])c1C(=O)NCc1ccccc1]

2-Nitro-6-methylbenzoic acid (0.91 g) and benzylamine (0.53 g) were dissolved in NMP (5 mL) and DIPEA (3 mL). HATU (1.9 g) was added and the mixture was stirred for 1 hour. The reaction mixture was diluted with ethyl acetate and washed with 1N hydrochloric acid, saturated aqueous sodium bicarbonate and then brine. The organic solution was dried with magnesium sulfate, filtered and the solvent was removed under vacuum to give a light brown oil (1.01 g) that crystallized on standing.

NMR (DMSO-$d_6$) δ 8.96 (t, 1H), 7.90 (d, 1H), 7.62 (d, 1H), 7.50 (t, 1H), 7.36-7.28 (m, 5H), 4.41 (d, 2H), 2.27 (s, 3H)

By proceeding in a similar manner the following compound was prepared from the appropriate starting materials:

Intermediate 20

N-Benzyl-2-fluoro-6-nitrobenzamide

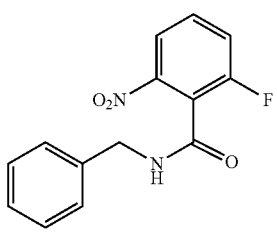 [SMILES: O=C(NCc1ccccc1)c1c(F)cccc1[N+](=O)[O-]]

Starting from 6-fluoro-2-nitrobenzoic acid and used without further characterisation.

Intermediate 21

N-(3-Bromo-2-cyanophenyl)-benzenesulfonamide

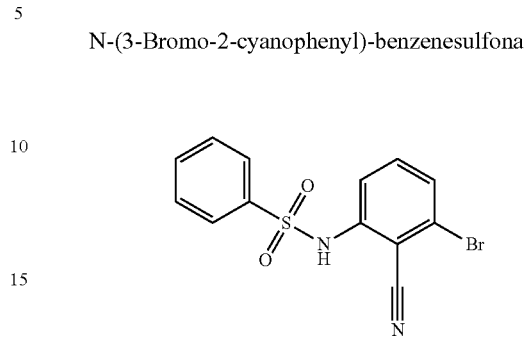

Benzenesulfonyl chloride (0.53 g) was added to a solution of 2-amino-6-bromobenzonitrile (Intermediate 22, 0.5 g) in DCM (15 mL) and pyridine (1 mL). The mixture was stirred for 2 hours, then a further aliquot of benzenesulfonyl chloride (0.53 g) was added and the mixture was stirred overnight. The reaction mixture was diluted with DCM, washed with 1N hydrochloric acid, and the organic solution was dried with sodium sulfate and filtered. The filtrate was evaporated under vacuum and the residue was purified by flash chromatography on silica, eluting with a mixture of DCM and methanol. The fractions containing the desired product were combined and evaporated to give the title compound as a white powder (0.24 g).

LCMS (Method E) r/t 3.33 min (M+H) 335, 337

Intermediate 22

2-Amino-6-bromobenzonitrile

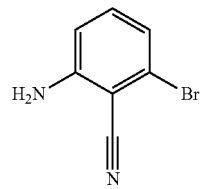

2-Bromo-6-nitrobenzonitrile (5 g) was dissolved in a solution of methanol (100 mL) and dioxane (65 mL) and heated to reflux. Iron powder (4.6 g) was added portion wise over 20 minutes and the mixture was heated at reflux for 4 hours. The mixture was allowed to cool to room temperature, filtered and the filtrate was evaporated under vacuum. The residue was triturated with water and the solid was collected by filtration to give the title compound as a light brown solid (3.8 g).

LCMS (Method E) r/t 3.01 min (M+H) 197, 199

Biological Activity

Compounds are tested for their capacity to inhibit recombinant human MetAP2 activity using the following assay.

Human recombinant Flag-MetAP2 expressed in Sf9 cells followed by affinity purification and EDTA treatment to remove endogenous active site cation was dialysed against $MnCl_2$ to produce the manganese enzyme used in the assay. The assay was carried out for 30 minutes at 25° C. in 50 mM HEPES buffer containing 100 mM NaCl, pH 7.5 the presence of 0.75 mM Methionine-Alanine-Serine (MAS) substrate and 50 μg/mL amino acid oxidase using a dilution of purified MetAP2 giving approximately 50,000 RFU control activity. Cleavage of the substrate by MetAP2 and oxidation of free methionine by amino acid oxidase was detected and quantified using fluorescence generated by Amplex red (10-acetyl-3,7-dihydroxyphenoxazine) in combination with horseradish peroxidase which detects $H_2O_2$ released during the oxidation step. The fluorescent signal was detected using a multiwell fluorimeter. Compounds were diluted in DMSO prior to addition to assay buffer, the final DMSO concentration in the assay being 1%.

The $IC_{50}$ is defined as the concentration at which a given compound achieves 50% inhibition of control. $IC_{50}$ values are calculated using the XLfit software package (version 2.0.5).

The compounds demonstrated activity in the assay of this Example as indicated in the following table, wherein A represents $IC_{50}<1$ μM and B represents $IC_{50}>1.0$ μM.

| Compound name | Activity |
|---|---|
| N-[1-(1H-Tetrazol-5-yl)-5,6,7,8-tetrahydronaphthalen-2-yl]-benzenesulfonamide | B |
| N-[3-Cyclopropyl-2-(1H-tetrazol-5-yl)-phenyl]-benzenesulfonamide | A |
| N-[3-Methoxy-2-(1H-tetrazol-5-yl)-phenyl]-benzenesulfonamide | A |
| N-[3-Methyl-2-(1H-tetrazol-5-yl)-phenyl]-benzenesulfonamide | B |
| N-[3-Bromo-2-(1H-tetrazol-5-yl)-phenyl]-benzenesulfonamide | B |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments have been discussed, the above specification is illustrative and not restrictive. Many variations will become apparent to those skilled in the art upon review of this specification. The full scope of the embodiments should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained.

What is claimed is:

1. The compounds N-[1-(1H-tetrazol-5-yl)-5,6,7,8-tetrahydronaphthalen-2-yl]-benzenesulfonamide, N-[3-cyclopropyl-2-(1H-tetrazol-5-yl)-phenyl]-benzenesulfonamide, N-[3-methoxy-2-(1H-tetrazol-5-yl)-phenyl]-benzenesulfonamide, N-[3-methyl-2-(1H-tetrazol-5-yl)-phenyl]-benzenesulfonamide, N-[3-bromo-2-(1H-tetrazol-5-yl)-phenyl]-benzenesulfonamide, and pharmaceutically acceptable salts thereof.

2. A pharmaceutical composition comprising a compound of claim 1, and a pharmaceutically acceptable carrier.

3. The composition of claim 2, wherein the composition is formulated as a unit dose.

4. The composition of claim 2, wherein the composition is formulated for oral administration.

5. The composition of claim 2, wherein the composition is formulated for intravenous or subcutaneous administration.

6. A method of inducing weight loss in a patient in need thereof, comprising administering to said patient a pharmaceutically effective amount of a compound of claim 1.

7. A method of treating and/or controlling obesity, comprising administering to a patient in need thereof an effective amount of a compound of claim 1.

8. The method of claim 7, wherein the patient is a human.

9. The method of claim 7, wherein the patient has a body mass index greater than or equal to about 30 kg/m² before the administration.

10. The method of claim 7, wherein the compound is administered orally or subcutaneously.

* * * * *